United States Patent
Gu et al.

(10) Patent No.: US 10,363,226 B2
(45) Date of Patent: Jul. 30, 2019

(54) PLATELET MEMBRANE-COATED DRUG DELIVERY SYSTEM

(71) Applicant: NORTH CAROLINA STATE UNIVERSITY, Raleigh, NC (US)

(72) Inventors: Zhen Gu, Apex, NC (US); Quanyin Hu, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/752,008

(22) PCT Filed: Aug. 12, 2016

(86) PCT No.: PCT/US2016/046655
§ 371 (c)(1),
(2) Date: Feb. 12, 2018

(87) PCT Pub. No.: WO2017/027760
PCT Pub. Date: Feb. 16, 2017

(65) Prior Publication Data
US 2018/0235894 A1    Aug. 23, 2018

Related U.S. Application Data

(60) Provisional application No. 62/204,084, filed on Aug. 12, 2015.

(51) Int. Cl.
*A61K 9/50* (2006.01)
*A61P 35/00* (2006.01)
(Continued)

(52) U.S. Cl.
CPC .......... *A61K 9/5068* (2013.01); *A61K 31/337* (2013.01); *A61K 31/4745* (2013.01);
(Continued)

(58) Field of Classification Search
None
See application file for complete search history.

(56) References Cited

U.S. PATENT DOCUMENTS 3,266,987 A    8/1966   Crowley et al.
3,960,757 A    6/1976   Morishita et al.
(Continued)

FOREIGN PATENT DOCUMENTS

WO    85/00968    3/1985
WO    87/02219    4/1987
WO    93/21906    11/1993

OTHER PUBLICATIONS

M Chen, J-G Geng. "P-selectin mediates adhesion of leukocytes, platelets, and cancer cells in inflammation, thrombosis, and cancer growth and metastasis." Archivum Immunologiae et Therapiae Experimentalis, vol. 54, 2006, pp. 75-84. (Year: 2006).*
(Continued)

*Primary Examiner* — Isaac Shomer
(74) *Attorney, Agent, or Firm* — Meunier Carlin & Curfman LLC

(57) ABSTRACT

Disclosed herein is a platelet membrane-coated nanovehicle having an inner core comprising a drug delivery matrix, and an outer shell platelet membrane coating the inner core. The inner core can be any drug delivery matrix capable of delivering a therapeutic agent to a cell. The outer shell platelet membrane can be a natural or synthetic membrane comprising platelet proteins capable of interacting with cancer cells. Also disclosed is a method for treating cancer in a subject that involves administering to the subject a platelet membrane-coated nanovehicle disclosed herein. Also disclosed is a method for treating vascular disease in a subject that involves administering to the subject a platelet membrane-coated nanovehicle disclosed herein.

17 Claims, 20 Drawing Sheets

(51) Int. Cl.
| | |
|---|---|
| A61K 45/06 | (2006.01) |
| A61K 31/337 | (2006.01) |
| A61K 31/4745 | (2006.01) |
| A61K 31/513 | (2006.01) |
| A61K 47/68 | (2017.01) |
| A61K 9/00 | (2006.01) |
| A61K 31/351 | (2006.01) |
| A61K 31/437 | (2006.01) |
| A61K 31/505 | (2006.01) |
| A61K 33/24 | (2019.01) |

(52) U.S. Cl.
CPC ............ *A61K 31/513* (2013.01); *A61K 45/06* (2013.01); *A61P 35/00* (2018.01); *A61K 9/0019* (2013.01); *A61K 31/351* (2013.01); *A61K 31/437* (2013.01); *A61K 31/505* (2013.01); *A61K 33/24* (2013.01); *A61K 47/6803* (2017.08); *A61K 2300/00* (2013.01); *Y10S 977/773* (2013.01); *Y10S 977/906* (2013.01)

(56) References Cited

U.S. PATENT DOCUMENTS

| | | | |
|---|---|---|---|
| 3,993,754 | A | 11/1976 | Rahman et al. |
| 4,145,410 | A | 3/1979 | Sears |
| 4,224,179 | A | 9/1980 | Schneider |
| 4,235,871 | A | 11/1980 | Papahadjopoulos et al. |
| 4,329,383 | A | 5/1982 | Joh |
| 4,460,563 | A | 7/1984 | Calanchi |
| 4,522,803 | A | 6/1985 | Lenk et al. |
| 4,588,578 | A | 5/1986 | Fountain et al. |
| 4,721,612 | A | 1/1988 | Janoff et al. |
| 4,794,000 | A | 12/1988 | Ecanow |
| 5,019,400 | A | 5/1991 | Gombotz |
| 6,143,211 | A | 11/2000 | Mathiowitz et al. |
| 6,620,617 | B2 | 9/2003 | Mathiowitz et al. |
| 2004/0243226 | A1 | 12/2004 | Rischell et al. |
| 2011/0052581 | A1* | 3/2011 | Karlin .............. A61K 31/44 424/133.1 |
| 2012/0009267 | A1 | 1/2012 | Cho et al. |
| 2013/0337066 | A1* | 12/2013 | Zhang ............. A61K 39/0011 424/489 |

OTHER PUBLICATIONS

TJ Merkel et al. "Using mechanobiological mimicry of red blood cells to extend circulation times of hydrogel nnicroparticles." Proceedings of the National Academy of Sciences, vol. 108 No. 2, Jan. 2011, pp. 586-591. (Year: 2011).*
JS Desgrosellier, DA Cheresh. "Integrins in cancer: biological implications and therapeutic opportunities." Nature Reviews Cancer, vol. 10, Jan. 2010, pp. 9-22. (Year: 2010).*
MJ Mitchell, E Wayne, K Rana, CB Schaffer, MR King. "TRAIL-coated leukocytes that kill cancer cells in the circulation." Proceedings of the National Academy of Sciences, vol. 111 No. 3, Jan. 2014, pp. 930-935. (Year: 2014).*
Aicher A, et al. (2003) Essential role of endothelial nitric oxide synthase for mobilization of stem and progenitor cells. Nature medicine 9(11):1370-1376.
Bagalkot V, Farokhzad OC, Langer R, & Jon S (2006) An Aptamer-Doxorubicin Physical Conjugate as a Novel Targeted Drug-Delivery Platform. Angewandte Chemie International Edition 45(48):8149-8152.
Bangham et al. (1965) Diffusion of univalent ions across the lamellae of swollen phospholipids.J. Mol. Biol., 13:238-252.
Beck et al., (1979) New long-acting injectable microcapsule contraceptive system Am J Obstet Gynecol 135(3):419-426.
Beck et al., (1979) A new long-acting injectable microcapsule system for the administration of progesterone. Fertil. Steril., 31:545.

Benita et al., (1984) Characterization of drug-loaded poly(d,l-lactide) microspheres. J. Pharm. Sci., 73:1721-1724.
Boilard E, et al. (2010) Platelets amplify inflammation in arthritis via collagen-dependent microparticle production. Science 327(5965):580-583.
Borsig L (2008) The role of platelet activation in tumor metastasis. University of Zurich, 31 pages. Expert Rev Anticancer Ther. 8(8):1247-55.
Borsig L, et al. (2001) Heparin and cancer revisited: mechanistic connections involving platelets, P-selectin, carcinoma mucins, and tumor metastasis. Proceedings of the National Academy of Sciences 98(6):3352-3357.
Chaffer CL & Weinberg RA (2011) A perspective on cancer cell metastasis. Science 331(6024):1559-1564.
Chambers AF, Groom AC, & MacDonald IC (2002) Metastasis: dissemination and growth of cancer cells in metastatic sites. Nature Reviews Cancer 2(8):563-572.
Cheng, Y., (2007) Dendrimers as drug carriers: applications in different routes of drug administration. J. Pharm. Sci. 97:123-143.
Chiu Y-L, et al. (2010) The characteristics, cellular uptake and intracellular trafficking of nanoparticles made of hydrophobically-modified chitosan. Journal of Controlled Release 146(1):152-159.
Cohen JA, et al. (2008) T-cell activation by antigen-loaded pH-sensitive hydrogel particles in vivo: the effect of particle size. Bioconjugate chemistry 20(1):111-119.
Copp JA, et al. (2014) Clearance of pathological antibodies using biomimetic nanoparticles. Proceedings of the National Academy of Sciences 111(37):13481-13486.
Cristofanilli M, et al. (2004) Circulating tumor cells, disease progression, and survival in metastatic breast cancer. New England Journal of Medicine 351(8):781-791.
Dai G & Patrono C (2007) Platelet activation and atherothrombosis. New England Journal of Medicine 357(24):2482-2494.
Deamer et al., (1970) Lamellar and hexagonal lipid phases visualized by freeze-etching Biochim. Biophys. Acta, 219:47-60.
Deamer et al., (1986) Permeability of lipid bilayers to water and ionic solutes. Chem. Phys. Lipids, 40:167-188.
Donovan LE, et al. (2013) Exploring the potential of the platelet membrane proteome as a source of peripheral biomarkers for Alzheimer's disease. Alzheimers Res Ther 5(32):10.1186.
Doshi N, et al. (2012) Platelet mimetic particles for targeting thrombi in flowing blood. Advanced Materials 24(28):3864-3869.
Fang RH, Aryal S, Hu C-MJ, & Zhang L (2010) Quick Synthesis of Lipid-Polymer Hybrid Nanoparticles with Low Polydispersity Using a Single-Step Sonication Method. Langmuir 26(22):16958-16962.
Fang RH, et al. (2014) Cancer cell membrane-coated nanoparticles for anticancer vaccination and drug delivery. Nano letters 14(4):2181-2188.
Farokhzad OC & Langer R (2009) Impact of nanotechnology on drug delivery. ACS nano 3(1):16-20.
Gao W, et al. (2015) Modulating Antibacterial Immunity via Bacterial Membrane-Coated Nanoparticles. Nano letters 15(2):1403-1409.
Gay LJ & Felding-Habermann B (2011) Contribution of platelets to tumour metastasis. Nature Reviews Cancer 11(2):123-134.
George D (2001) Platelet-derived growth factor receptors: a therapeutic target in solid tumors. Seminars in oncology, (Elsevier), pp. 27-33.
Hu C-MJ, et al. (2011) Erythrocyte membrane-camouflaged polymeric nanoparticles as a biomimetic delivery platform. Proceedings of the National Academy of Sciences 108(27):10980-10985.
Hu C-MJ, Fang RH, Copp J, Luk BT, & Zhang L (2013) A biomimetic nanosponge that absorbs pore-forming toxins. Nature nanotechnology 8(5):336-340.
Hu C-MJ, Fang RH, Luk BT, & Zhang L (2013) Nanoparticle-detained toxins for safe and effective vaccination. Nature nanotechnology 8(12):933-938.
Hu Q, et al. (2013) F3 peptide-functionalized PEG-PLA nanoparticles co-administrated with tLyp-1 peptide for anti-glioma drug delivery. Biomaterials 34(4):1135-1145.
Jiang T, et al. (2014) Furin-Mediated Sequential Delivery of Anti-cancer Cytokine and Small-Molecule Drug Shuttled by Graphene. Advanced Materials 27(6): 1021-1028.

(56) References Cited

OTHER PUBLICATIONS

Jiang T, Mo R, Bellotti A, Zhou J, & Gu Z (2014) Gel-Liposome-Mediated Co-Delivery of Anticancer Membrane-Associated Proteins and Small-Molecule Drugs for Enhanced Therapeutic Efficacy. Advanced Functional Materials 24(16):2295-2304.
Jurasz P, Alonso-Escolano D, & Radomski MW (2004) Platelet-cancer interactions: mechanisms and pharmacology of tumour cell-induced platelet aggregation. British journal of pharmacology 143(7):819-826.
Koivusalo M, et al. (2010) Amiloride inhibits macropinocytosis by lowering submembranous pH and preventing Rac1 and Cdc42 signaling. The Journal of cell biology 188(4):547-563.
Labelle M, Begum S, & Hynes RO (2011) Direct signaling between platelets and cancer cells induces an epithelial-mesenchymal-like transition and promotes metastasis. Cancer cell 20(5):576-590.
Labelle M, Begum S, & Hynes RO (2014) Platelets guide the formation of early metastatic niches. Proceedings of the National Academy of Sciences 11(30):E3053-E3061.
Liu X, et al. (2014) Platelet-inspired Multiscaled Cytophilic Interfaces with High Specificity and Efficiency toward Point-of-Care Cancer Diagnosis. Small 10(22):4677-4683.
Mathiowitz et al., (1990) Morphology of polyanhydride microsphere delivery systems. J. Scanning Microscopy, 4:329-340.
Mathiowitz et al., (1987) Novel microcapsules for delivery systems. Reactive Polymers, 6:275.
Mitchell MJ, Wayne E, Rana K, Schaffer CB, & King MR (2014) TRAIL-coated leukocytes that kill cancer cells in the circulation. Proceedings of the National Academy of Sciences 111(3):930-935.
Mo R, et al. (2012) Multistage pH-Responsive Liposomes for Mitochondrial-Targeted Anticancer Drug Delivery. Advanced Materials 24(27):3659-3665.
Mo R, Jiang T, DiSanto R, Tai W, & Gu Z (2014) ATP-triggered anticancer drug delivery. Nature communications 5:3364.
Nash G, Turner L, Scully N, & Kakkar A (2002) Platelets and cancer. The lancet oncology 3(7):425-430.
Nguyen DX, Bos PD, & Massagué J (2009) Metastasis: from dissemination to organ-specific colonization. Nature Reviews Cancer 9(4):274-284.
Papahadjopoulos et al. (1967) Phospholipid model membranes. I. Structural characteristics of hydrated liquid crystals. Biochim. Biophys, Acta., 1967, 135:624-638.
Parodi A, et al. (2013) Biomimetic functionalization with leukocyte membranes imparts cell like functions to synthetic particles. Nature nanotechnology 8(1):61.
Peer D, et al. (2007) Nanocarriers as an emerging platform for cancer therapy. Nature nanotechnology 2(12):751-760.
Popielarski SR, Pun SH, & Davis ME (2005) A nanoparticle-based model delivery system to guide the rational design of gene delivery to the liver. 1. Synthesis and characterization. Bioconjugate chemistry 16(5):1063-1070.
Price JE, Polyzos A, Zhang RD, & Daniels LM (1990) Tumorigenicity and metastasis of human breast carcinoma cell lines in nude mice. Cancer research 50(3):717-721.
Qureshi AH, et al. (2009) Proteomic and phospho-proteomic profile of human platelets in basal, resting state: insights into integrin signaling. PLoS One 4(10):e7627.
Rehman Z, et al. (2011) Protein kinase A inhibition modulates the intracellular routing of gene delivery vehicles in HeLa cells, leading to productive transfection. Journal of Controlled Release 156(1):76-84.
Ruggeri ZM (2002) Platelets in atherothrombosis. Nature medicine 8(11): 1227-1234.
Sarikaya M, Tamerler C, Jen AK-Y, Schulten K, & Baneyx F (2003) Molecular biomimetics: nanotechnology through biology. Nature materials 2(9):577-585.
Sheridan C, et al. (2006) CD44+/CD24-breast cancer cells exhibit enhanced invasive properties: an early step necessary for metastasis. Breast Cancer Res 8(5):R59.
Stone J & Wagner D (1993) P-selectin mediates adhesion of platelets to neuroblastoma and small cell lung cancer. Journal of Clinical Investigation 92(2):804.
Sun W, et al. (2014) Cocoon-Like Self-Degradable DNA Nanoclew for Anticancer Drug Delivery. Journal of the American Chemical Society 136(42):14722-14725.
Svenson, S., (2009) Dendrimers as versatile platform in drug delivery applications. Eur J Pharm Biopharm 71:445-462.
Szoka, Jr. et al., (1980) Comparative properties and methods of preparation of lipid vesicles (liposomes). Ann. Rev. Biophys. Bioeng., 9:467.
Wang Q, et al. (2014) Non-genetic engineering of cells for drug delivery and cell-based therapy. Advanced drug delivery reviews.
Yoo J-W, Irvine DJ, Discher DE, & Mitragotri S (2011) Bio-inspired, bioengineered and biomimetic drug delivery carriers. Nature reviews Drug discovery 10(7):521-535.
Zhang X-X, et al. (2011) Macropinocytosis is the Major Pathway Responsible for DNA Transfection in CHO cells by a Charge-Reversal Amphiphile. Molecular pharmaceutics 8(3):758-766.
Ding, et al., (2006) Advanced Drug Delivery Systems that Target the Vascular Endothelium, Molecular Intervationss, 98-112.
International Search Report and Written Opinion issued for Application No. PCT/US2016/046655, dated Oct. 26, 2016.
International Preliminary Report on Patentability issued for Application No. PCT/US2016/046655, dated Feb. 22, 2018.

* cited by examiner

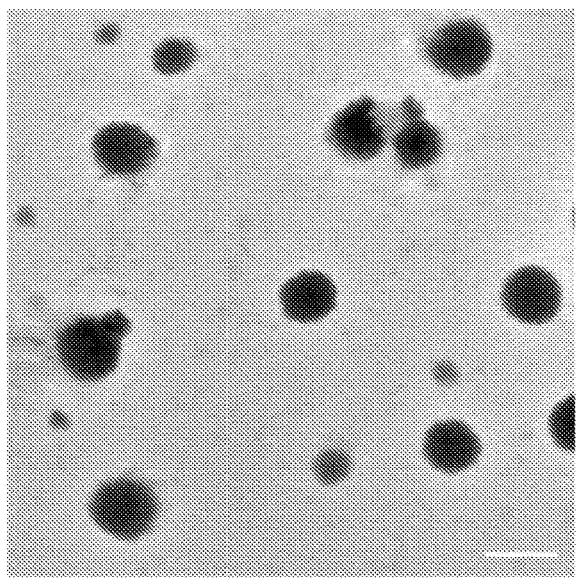
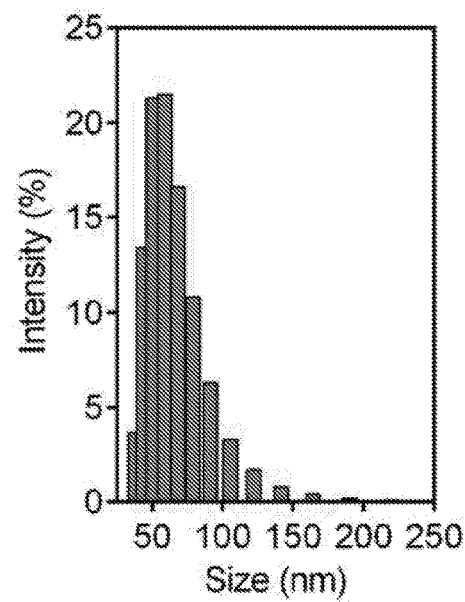
FIG 8A
FIG 8B
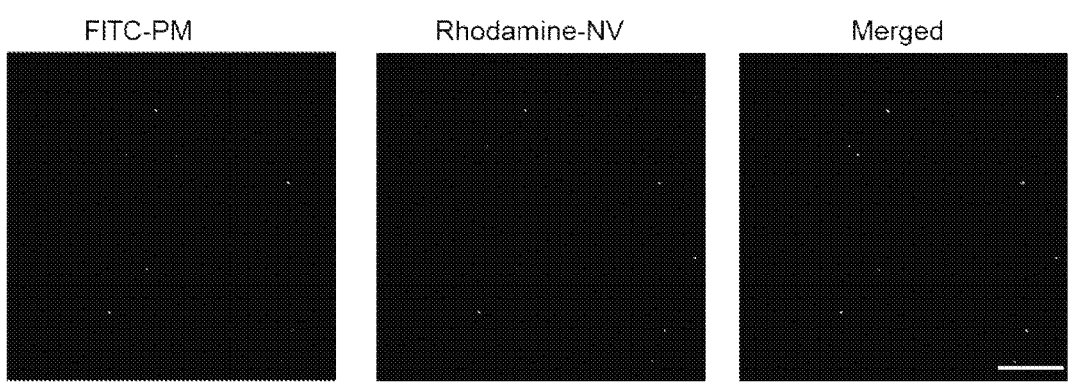
FIG 9

| Parameter | Dox-NV | Dox-PM-NV |
|---|---|---|
| AUC (μg/mL/h)$_{0-t}$ | 2963.3±964.3 | 112766.2±5251.4*** |
| $T_{1/2}$ (h) | 5.6±1.4 | 32.6±2.7*** |
| CL(L/h) | 1.8±0.7 | 0.04±0.001*** |

$AUC_{0-t}$: Area under plasma Dox concentration versus time curves $T_{1/2}$: Elimination half-life CL: *In vivo* clearance rate

PLATELET MEMBRANE-COATED DRUG DELIVERY SYSTEM

CROSS-REFERENCE TO RELATED APPLICATIONS

This application is a national stage application filed under 35 U.S.C. § 371 of PCT/US 2016/046655 filed Aug. 12, 2016, which claims benefit of U.S. Provisional Application No. 62/204,084, filed Aug. 12, 2015, each of which are hereby incorporated herein by reference in its entirety.

STATEMENT REGARDING FEDERALLY SPONSORED RESEARCH OR DEVELOPMENT

This invention was made with Government Support under Grant No. TR001111 awarded by the National Institutes of Health. The Government has certain rights in the invention.

BACKGROUND

Biomimetic drug delivery system offers new opportunities to mimic the biological particulates, including cells, vesicles and viruses for enhancing biocompatibility and promoting therapeutic efficacy (Sarikaya M, et al. (2003) Nat Mater. 2(9):577-585; Yoo J-W, et al. (2011) Nat Rev Drug Discov. 10(7):521-535; Gao W, et al. (2015) Nano letters 15(2):1403-1409; Wang Q, et al. (2014) Adv Drug Deliv Rev). As a simple and effective biomimetic approach, delivery vehicles coated with cell membranes are currently being intensely pursued to achieve a variety of merits, such as prolonging circulation time, alleviating immunogenicity and achieving active targeting ability. Typical examples include red blood cell (RBC) membrane-coated PLGA nanoparticles (Hu C-M J, et al. (2011) Proc Natl Acad Sci USA. 108(27):10980-10985; Hu C-MJ, et al. (2013) Nat Nanotechnol. 8(5):336-340; Hu C-M J, et al. (2013) Nat Nanotechnol. 8(12):933-938; Copp J A, et al. (2014) Proc Natl Acad Sci USA. 111(37):13481-13486), white blood cell (WBC) membrane-decorated silica particles (Parodi A, et al. (2013) Nat Nanotechnol. 8(1):61) and cancer cell membrane-cloaked nanoparticles (Fang R H, et al. (2014) Nano letters 14(4):2181-2188). However, suitable drug delivery systems targeting cancer cells have yet to be developed.

SUMMARY

Disclosed herein is a platelet membrane-coated core-shell nanovehicle ("PM-NV"), which can sequentially and site-specifically deliver both extracellularly active drugs and intracellularly functional drugs to cancer cells. By taking advantage of the high affinity between PM and cancer cells, the PM-NV effectively aggregates on the surface of cancer cells and can thereby promote the interaction of extracellularly active drugs. After endocytosis, PM-NVs can be degraded by acidity in the lyso-endosome, accompanied by the release and further accumulation of encapsulated intracellularly functional drugs. Furthermore, PM-NV can eliminate the circulating tumor cells (CTCs) in vivo and significantly inhibit the tumor metastasis. Moreover, since platelets also play a key role in several physiologic and pathologic processes such as hemostasis and thrombosis by forming the plugs that seal injured vessels and arrest bleeding, this platform can also be used to treat vascular relevant diseases.

Therefore, disclosed herein is a platelet membrane-coated nanovehicle having an inner core comprising a drug delivery matrix, and an outer shell platelet membrane coating the inner core. The inner core can be any drug delivery matrix capable of delivering a therapeutic agent to a cell. For example, the therapeutic agent can be hydrophilic or hydrophobic small molecule compound. In some cases, the therapeutic agent is an intracellularly active small molecule drug that is released from the inner core inside the cell. For example, the drug can be a hydrophobic or hydrophilic anti-neoplastic drug.

The outer shell platelet membrane can be a natural or synthetic membrane comprising platelet proteins capable of interacting with cancer cells. In some cases, the platelet membrane is produced by lysing platelets, such as autologous platelets from the subject to be treated. In other cases, the outer shell is a synthetic membrane, such as a liposome, engineered to contain platelet proteins capable of interacting with cancer cells. For example, the outer shell platelet membrane can comprise P-selectin protein. The shell platelet membrane can comprise integrin $\alpha_{IIb}\beta_3$. The shell platelet membrane can comprise a self-recognized immunomodulatory protein selected from the group consisting of CD47, CD55, and CD59.

Whether natural or synthetic, the outer shell platelet membrane can be engineered to include at least one heterologous extracellularly active protein. This extracellularly active protein can be any protein, natural or synthetic, that will have a therapeutic effect when in contact with a cancer cell. For example, the extracellularly active protein can be a tumor necrosis factor (TNF)-related apoptosis inducing ligand (TRAIL), which can bind the DR4 and DR5 death receptors on tumor cells and induce apoptosis. As another example, the extracellularly active protein can be a therapeutic antibody, such as Cetuximab, Trastuzumab, Bevacizumab, Panitumumab, Ipilimumab, Rituximab, Alemtuzumab, Ofatumumab, Gemtuzumab ozogamicin, Brentuximab vedotin, Pembrolizumab (Keytruda), nivolumab (Opdivo), or a combination thereof.

Also disclosed is a method for treating cancer in a subject that involves administering to the subject a platelet membrane-coated nanovehicle disclosed herein. In some cases, the platelet membrane is autologous, i.e., produced from a platelet obtained from the subject. In some cases, the method can be used to treat any cancer that overexpresses CD44. Therefore, in some cases, the method further involves assaying a sample from the subject for CD44 expression, and treating the subject with the disclosed platelet membrane-coated nanovehicle if elevated CD44 levels are detected. In some cases, the cancer is a circulating cancer cell. In some cases, the cancer is a metastatic cancer cell.

Also disclosed is a method for treating vascular disease in a subject that involves administering to the subject a platelet membrane-coated nanovehicle disclosed herein. In these embodiments, the drug delivery matrix encapsulates a drug to treat vascular disease, e.g., coagulation or coronary restenosis. For example, the drug can be heparin or doxorubicin.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows the main components of TRAIL-Dox-PM-NV: TRAIL-conjugated platelets membrane derived from platelets; Dox-loaded nanovehicle (Dox-NV). I: centrifugation of whole blood; II: isolation of platelets; III: extraction of platelets membrane. FIG. 1B illustrates in vivo elimination of circulating tumor cells (CTCs) and sequential delivery of TRAIL and Dox. TRAIL-Dox-PM-NV captured the CTCs via specific affinity of P-Selectin and overexpressed CD44 receptors and subsequently triggered TRAIL/Dox-induced apoptosis signaling pathway. I: the interaction of TRAIL and death receptors (DRs) to trigger the apoptosis signaling; II: the internalization of TRAIL-Dox-PM-NV; III: the dissociation of TRAILDox-PM-NV mediated by the acidity of lyso-endosome; IV: release and accumulation of Dox in the nuclei; V: intrinsic apoptosis triggered by Dox.

FIG. 2A is a TEM image and bar graph showing hydrodynamic size distribution of PMNV. Arrow indicates the existence of platelet membrane. The scale bar: 100 nm; inset: 50 nm. FIG. 2B contains bar graphs showing changes in particle size and zeta potential of NV after coating with PM. Error bars indicate s.d. (n=3). FIG. 2C is a graph showing in vitro stability of NV and PM-NV in the 100% fetal bovine serum. The absorbance at 560 nm is monitored. Error bars indicate s.d. (n=3). FIG. 2D is a graph showing in vitro release of Dox from NV and PM-NV in PBS with different pH. Error bars indicate s.d. (n=3).

FIG. 3A shows extracellular distribution of NV and PM-NV after 2 h incubation. White arrows indicate the location of rhodamine-labeled NV and PM-NV. Scale bar: 20 μm. FIG. 3B shows the induced apoptosis of MDA-MB-231 cells treated with TRAIL-Dox-NV and TRAIL-DoxPM-NV after incubation for 12 h using the APO-BrdU TUNEL assay. Fluorescence indicates Alexa Fluor 488-stained nick end label DNA fragment, and PI-stained nuclei. Scale bar: 100 μm. FIG. 3C shows intracellular delivery of TRAIL-Dox-PM-NV on MDA-MB-231 cells at different time observed by CLSM. The late endo-lysosomes were stained by LysoTracker Green, and the nuclei were stained by Hoechst 33342. Scale bar: 20 μm. FIG. 3D shows flow cytometry analysis of MDA-MB-231 cells after staining with Annexin V-FITC and PI. The cells were treated with TRAIL-Dox-NV, TRAIL-PM-NV, Dox-PM-NV and TRAIL-Dox-PM-NV at the TRAIL concentration of 20 ng/mL and Dox concentration of 200 ng/mL for 12 h. The cells incubated with drug-free DMEM were served as a control. FIG. 3E shows in vitro cytotoxicity of TRAIL-Dox-NV, TRAIL-PMNV, Dox-PM-NV and TRAIL-Dox-PM-NV after incubation for 24 h. Error bars indicate s.d. (n=3).

FIG. 4A shows in vivo fluorescence imaging of the MDA-MB-231 tumor-bearing nude mice at 6, 12, 24 h and 48 h after intravenous injection of Cy5.5-labeled TRAIL-Dox-NV (i) and Cy5.5-labeled TRAIL-DoxPM-NV (ii) at Cy5.5 dose of 20 nmol/kg. Arrows indicate the sites of tumors. FIG. 4B shows ex vivo fluorescence imaging of the excised tumors and normal tissues at 48 h post injection. i, Cy5.5-TRAIL-Dox-NV; ii, Cy5.5-TRAIL-Dox-PM-NV. From top to bottom, 1: tumor; 2: kidney; 3: lung; 4: spleen; 5: liver; 6: heart. FIG. 4C shows region-of-interest analysis of fluorescent intensities from the tumors and normal tissues. Error bars indicate s.d. (n=3). *P<0.05 (two-tailed Student's t-test). FIG. 4D shows in vivo fluorescence images of tumors treated with TRAIL-Dox-NV and TRAIL-Dox-PM-NV. Scale bar: 100 μm.

FIG. 5A shows representative images of the MDA-MB-231 tumors after treatment with different TRAIL/Dox formulations at day 16 (from top to bottom, 1: saline, 2: TRAILDox-NV, 3: TRAIL-PM-NV, 4: Dox-PM-NV, 5: TRAIL-Dox-PM-NV) at TRAIL dose of 1 mg/kg and Dox dose of 2 mg/kg. FIG. 5B shows MDA-MB-231 tumor growth curves after intravenous injection of different TRAIL/Dox formulations. Error bars indicate s.d. (n=5). *P<0.05 (two-tailed Student's t-test). FIG. 5C shows body weight variation of MDA-MB-231 tumor-bearing mice during the treatment. Error bars indicate s.d. (n=5). FIG. 5D shows histological observation and detection of apoptosis in the tumor tissues after treatment. The tumor sections were stained with hematoxylin and eosin, fluorescein-dUTP for apoptosis and Hoechst for nuclei. The numeric label for each tumor is as follows: 1, saline; 2, TRAIL-Dox-NV; 3, TRAIL-PMNV; 4, Dox-PM-NV; 5, TRAIL-Dox-PM-NV. Scale bar: 100 μm.

FIG. 6A shows representative images of the lung tissues 8 weeks post intravenous injection with MDA-MB-231 cells and different TRAIL/Dox formulations. Red arrows indicate the visible metastatic nodules. FIG. 6B shows histological observation of the lung tissues after treatment. The lung sections were stained with hematoxylin and eosin. Black arrows indicate the tumor cells. Scale bar: 200 μm. FIG. 6C shows quantification of visible metastatic nodules. i: Saline; ii: TRAILDox-NV; TRAIL-Dox-PM-NV. Error bars indicate s.d. (n=3). ***P<0.001 (two-tailed Student's t-test).

FIGS. 8A and 8B show characterization of NV via DLS and TEM. FIG. 8A is a TEM image of NV. Scale bar, 100 nm. FIG. 8B shows hydrodynamic size distribution of NV.

FIG. 9 shows CLSM images of PM-NV. NV was labeled with rhodamine and PM was labeled with FITC for imaging. Scale bar: 50 μm.

FIG. 11A shows fluorescence images of the uptake of Dox-NV and Dox-PM-NV at Dox concentration of 200 ng/mL. Scale bar: 50 μm. FIG. 11B shows quantification of uptake efficiency of Dox-NV and Dox-PM-NV using flow cytometry.

FIG. 12A shows the plasma Dox concentration curves of the Dox-NV and Dox-PM-NV. Error bars indicated s.d. (n=3). FIG. 12B shows pharmacokinetic parameters of the Dox-NV and Dox-PN-NV. ***P<0.001 (two-tailed Student's t-test).

DETAILED DESCRIPTION

Given the complexity of biological entities with different sorts of membranes integrated with distinct bioactive components, versatile biomimetic drug delivery systems with high specificity are expected to develop. Platelet is an indispensable component of blood stream with the ability of targeting vascular injury sites to impede thrombogenesis and maintaining the integrity of blood circulation (Doshi N, et al. (2012) Adv Mater. 24(28):3864-3869; Liu X, et al. (2014) Small 10(22):4677-4683; Gay L J & Felding-Habermann B (2011) Nat Rev Cancer. 11(2):123-134; Nguyen D X, et al. (2009) Nat Rev Cancer. 9(4):274-284). Recently, the recognition and interaction between platelets and circulating tumor cells in blood have aroused considerable attention because of its crucial contribution to tumor metastasis (Nash G, et al. (2002) Lancet Oncol. 3(7):425-430; Labelle M, et al. (2011) Cancer Cell 20(5):576-590). The aggregation of platelets surrounding circulating tumor cells (CTCs) helps CTCs survive in blood stream and spread to new tissues (Chaffer C L & Weinberg R A (2011) Science 331(6024): 1559-1564). The mechanism underlying this specific aggregation includes biomolecular binding such as P-Selectin and CD44 receptors (Borsig L, et al. (2001) Proc Natl Acad Sci USA. 98(6):3352-3357; Stone J & Wagner D (1993) J Clin Invest. 92(2):804) and structure-based capture (Jurasz P, et al. (2004) Br J Pharmacol. 143(7):819-826; Labelle M, et al. (2014) Proc Natl Acad Sci USA. 111(30):E3053-E3061).

Figure 1A:
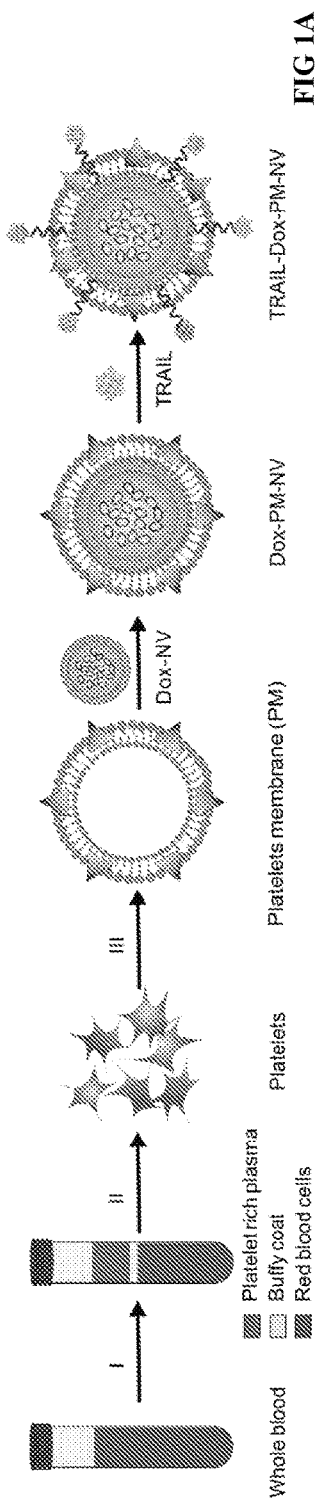
FIGS. 1A and 1B show a schematic design of drug-loaded PM-NV for targeting and sequential drug delivery.

Disclosed herein is a platelet membrane-coated core-shell nanovehicle ("PM-NV") for targeting and sequential, site-specific delivery of extracelluarly active proteins and intracellular functional small molecular drugs. As displayed in FIG. 1A, the PM-NV can be composed of two components: 1) an inner core part for loading intracellular functional drugs; and 2) the platelet membrane based outer shell for decoration of extracelluarly active proteins. The platelet membranes can be derived from platelet and purified to coat the surface of NV. Equipped with large numbers of "self-recognized" proteins, this PM-NV is expected to minimize the in vivo immunogenicity, prolong the circulation time (George D (2001) Seminars in oncology, (Elsevier), pp 27-33). More importantly, the overexpressed P-Selectin on the PM can specifically bind to CD44 receptors upregulated on the surface of cancer cells. Taken together, the PM-NV could actively target to tumor site and sequentially deliver anticancer therapeutics to their most active destinations.

As an example, a PM-NV was produced using two anticancer therapeutics—TRAIL and Dox (designated "TRAIL-Dox-PM-NV"). As one of the most important extracellular activators of apoptosis, TRAIL induces apoptosis of tumor cells by binding to the death receptors (DR4, DR5) on the cell surface (Jiang T, et al. (2014) Adv. Functional Mater. 24(16):2295-2304; Jiang T, et al. (2014) Adv Mater. 27(6):1021-8); while Dox can intercalate the nuclear DNA of cancer cells to trigger the intrinsic apoptosis signaling pathway (Mo R, et al. (2014) Nat Commun. 5:3364; Sun W, et al. (2014) J Am Chem Soc. 136(42): 14722-14725; Bagalkot V, et al. (2006) Angew Chem Int Ed Engl. 45(48):8149-8152).

Figure 1B:
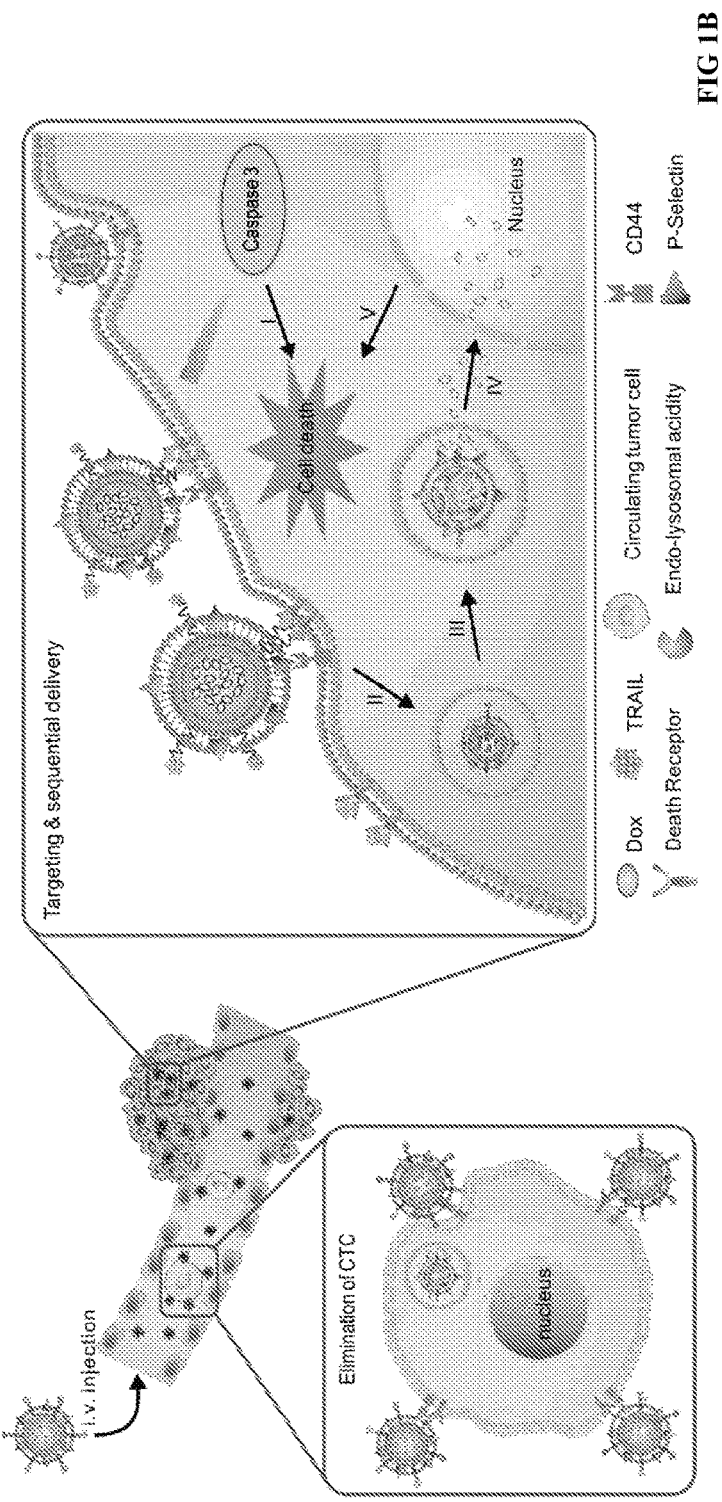

After intravenous (i.v.) injection, the PM-NVs are expected to accumulate in the tumor site by combination of the passive enhanced permeability and retention (EPR) effect (Peer D, et al. (2007) Nat Nanotechnol. 2(12):751-760; Farokhzad O C & Langer R (2009) ACS nano 3(1): 16-20) and active targeting based on the affinity between PM and overexpressed CD44 receptors on the cancer cells (FIG. 1B). Meanwhile, the aggregation of PM-NV on the surface of cancer cells enabled by capture ability of P-Selectin could facilitate the interaction between TRAIL and cell membranes and subsequently initiation of extrinsic apoptosis signaling. Additionally, the affinity of P-Selectin and CD44 are also expected to readily eliminate CTCs (FIG. 1B), which plays a vital role in tumor metastasis (Mitchell M J, et al. (2014) Proc Natl Acad Sci USA. 111(3):930-935; Cristofanilli M, et al. (2004) N Engl J Med. 351(8):781-791; Chambers A F, et al. (2002) Nat Rev Cancer. 2(8):563-572). After cellular internalization, the acidity in the endo-lysosome is expected to digest the acid-responsive modality in the PM-NV, accompanied by the release of encapsulated Dox, which will accumulate in the nuclei of cancer cells for synergistically inducing apoptosis.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "sample from a subject" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Nonlimiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "small molecule" refers to a molecule, such as an organic or organometallic compound, with a molecular weight of less than 2,000 Daltons, more preferably less than 1,500 Daltons, most preferably less than 1,000 Daltons. The small molecule can be a hydrophilic, hydrophobic, or amphiphilic compound.

The term "drug" refers to a compound (or mixture of different compounds) that can be used to effect a physiological change in a subject. As used herein, drugs include small molecule, polypeptides and nucleic acids.

A "liposome" is a small vesicle composed of various types of lipids, phospholipids and/or surfactant which is useful for delivery of a drug (such as the antagonists disclosed herein and, optionally, a chemotherapeutic agent) to a mammal. The components of the liposome are commonly arranged in a bilayer formation, similar to the lipid arrangement of biological membranes.

The term "nanoparticle" refers to any particles having dimensions in the 1-1,000 nm range which solubilize and stabilize ITC. In some embodiments, nanoparticles have dimensions in the 2-200 nm range, preferably in the 2-150 nm range, and even more preferably in the 2-100 nm range. Nanoparticles used in the present invention include such nanoscale materials as a polymer-based nanoparticle, lipid-based nanoparticle, an emulsion, a hydrogel, a micelle, and the like.

Nanovehicle

The disclosed platelet membrane-coated nanovehicle have diameters of less than about 5000 nm, such as less than about 4000 nm, less than about 3000 nm, less than about 2000 nm, from about 10 nm to about 2000 nm, from about 20 nm to about 2000 nm, from about 50 nm to about 2000 nm, from about 100 nm to about 2000 nm, from about 200 nm to about 2000 nm, from about 250 nm to about 2000 nm, from about 300 nm to about 2000 nm, from about 350 nm to about 2000 nm, from about 400 nm to about 2000 nm, from about 10 nm to about 1000 nm, from about 20 nm to about 1000 nm, from about 50 nm to about 1000 nm, from about 100 nm to about 1000 nm, from about 200 nm to about 1000 nm, from about 250 nm to about 1000 nm, from about 300 nm to about 1000 nm, from about 350 nm to about 1000 nm, from about 400 nm to about 1000 nm, less than 5000 nm, less than 4000 nm, less than 3000 nm, less than 2000 nm, from 10 nm to 2000 nm, from 20 nm to 2000 nm, from 50 nm to 2000 nm, from 100 nm to 2000 nm, from 200 nm to 2000 nm, from 250 nm to 2000 nm, from 300 nm to 2000 nm, from 350 nm to 2000 nm, from 400 nm to 2000 nm, from 10 nm to 1000 nm, from 20 nm to 1000 nm, from 50 nm to 1000 nm, from 100 nm to 1000 nm, from 200 nm to 1000 nm, from 250 nm to 1000 nm, from 300 nm to 1000 nm, from 350 nm to 1000 nm, from 400 nm to 1000 nm, etc. The shapes of the particles are not particularly critical: spherical particles are typical. Where non-spherical nanoparticles are employed, "diameter" is meant to refer to the diameter of a hypothetical sphere having the same volume of the non-spherical nanoparticle. For the purposes of the present invention, "a substantial portion" of the nanoparticles are to be deemed to have a specified diameter or a specified range of diameters when more than 50% (e.g., more than 60%, more than 65%, more than 70%, more than 75%, more than 80%, more than 85%, more than 90%, etc.) have diameters of the specified diameter or within the specified range of diameters.

Zeta potential is another important parameter that is related to nanoparticle stability or aggregation in a dispersion, and can have significant implications on product performance. The disclosed platelet membrane-coated nanovehicle can have an average zeta potential (surface charge) of from −1 mV to −40 mV, including about −1, −2, −3, −4, −5, −6, −7, −8, −9, −10, −11, −12, 13, −14, −15, −16, −17, −18, −19, −20, −21, −22, −23, −24, −25, −26, −27, −28, −29, −30, −31, −32, −33, 34, −35, −36, −37, −38, −39, or −40 mV.

The disclosed platelet membrane-coated nanovehicle has an inner core comprising a drug delivery matrix, and an outer shell platelet membrane coating the inner core.

Inner Core

The inner core can be any drug delivery matrix capable of encapsulating and delivering a therapeutic agent to a cell. For example, the drug delivery matrix can be a polymeric gel particle, lipid particle, or inorganic particle. In some case, the drug delivery matrix is biodegradable. In some cases, the drug delivery matrix is pH sensitive.

The nanovehicles may be combined with platelet membranes by combining lysed platelet membrane, or synthetic membrane components, with the inner core. In some embodiments, the components may be combined in a solvent. In certain embodiments, a hydrophilic inner core is used. When a hydrophobic inner core is used, the outer surface of the inner core can be chemically functionalize with hydrophilic functional groups to facilitate coating with the platelet membrane. In some embodiments, the nanovehicle can be functionalized with a hydrophilic group in order to facilitate incorporation into the platelet membrane.

Polymeric Gel Particle

Particles can be made from one or more polymers. In some examples, the polymer includes copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic) acid, poly(lactic coglycolic) acid (PLGA), cellulose derivatives, such as hydroxymethylcellulose, hydroxypropylcellulose and the like. In one example, the polymer is 50:50 PLGA copolymer. In other examples, the polymer includes a natural polymer, such as chitosan, collagen, alginate, gelatin, hyaluronic acid, and nontoxic metal salts thereof. In some embodiments the polymer is a hydrogel, for example an alginate hydrogel. Hydrophilic polymers and other vehicles can be used alone or in combination, and enhanced structural integrity can be imparted to the vehicle by partial crystallization, ionic bonding, cross-linking and the like.

Methods of encapsulating drugs into particles are known in the art. Common encapsulation techniques include, but are not limited to, spray drying, interfacial polymerization, hot melt encapsulation, phase separation encapsulation (spontaneous emulsion microencapsulation, solvent evaporation microencapsulation, and solvent removal microencapsulation), coacervation, low temperature microsphere formation, and phase inversion nanoencapsulation (PIN). A brief summary of these methods is presented below.

In certain embodiments, the nanoparticles incorporated in the compositions discussed herein are multi-walled nanoparticles. Multi-walled nanoparticles useful in the compositions disclosed herein can be prepared, for example, using "sequential phase inversion nanoencapsulation" (sPIN).

1. Spray Drying

Methods for forming microspheres/nanospheres using spray drying techniques are described in U.S. Pat. No. 6,620,617, to Mathiowitz et al. In this method, the polymer is dissolved in an organic solvent such as methylene chloride or in water. A known amount of one or more active agents to be incorporated in the particles is suspended (in the case of an insoluble active agent) or co-dissolved (in the case of a soluble active agent) in the polymer solution. The solution or dispersion is pumped through a micronizing nozzle driven by a flow of compressed gas, and the resulting aerosol is suspended in a heated cyclone of air, allowing the solvent to evaporate from the microdroplets, forming particles. Microspheres/nanospheres ranging between 0.1-10 microns can be obtained using this method.

2. Interfacial Polymerization

Interfacial polymerization can also be used to encapsulate one or more active agents. Using this method, a monomer and the active agent(s) are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

3. Hot Melt Micro Encapsulation

Microspheres can be formed from polymers such as polyesters and polyanhydrides using hot melt microencapsulation methods as described in Mathiowitz et al., Reactive Polymers, 6:275 (1987). In this method, the use of polymers with molecular weights between 3-75,000 daltons is preferred. In this method, the polymer first is melted and then mixed with the solid particles of one or more active agents to be incorporated that have been sieved to less than 50 microns. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microspheres are washed by decanting with petroleum ether to give a free-flowing powder.

4. Phase Separation Microencapsulation

In phase separation microencapsulation techniques, a polymer solution is stirred, optionally in the presence of one or more active agents to be encapsulated. While continuing to uniformly suspend the material through stirring, a non-solvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

i. Spontaneous Emulsion Microencapsulation

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

ii. Solvent Evaporation Microencapsulation

Methods for forming microspheres using solvent evaporation techniques are described in E. Mathiowitz et al., J. Scanning Microscopy, 4:329 (1990); L. R. Beck et al., Fertil. Steril., 31:545 (1979); L. R. Beck et al Am J Obstet Gynecol 135(3) (1979); S. Benita et al., J. Pharm. Sci., 73:1721 (1984); and U.S. Pat. No. 3,960,757 to Morishita et al. The polymer is dissolved in a volatile organic solvent, such as methylene chloride. One or more active agents to be incorporated are optionally added to the solution, and the mixture is suspended in an aqueous solution that contains a surface active agent such as poly(vinyl alcohol). The resulting emulsion is stirred until most of the organic solvent evaporated, leaving solid microspheres/nanospheres. This method is useful for relatively stable polymers, such as polyesters and polystyrene. However, labile polymers, such as polyanhydrides, may degrade during the fabrication process due to the presence of water. For these polymers, some of the following methods performed in completely anhydrous organic solvents are more useful.

iii. Solvent Removal Microencapsulation

The solvent removal microencapsulation technique is primarily designed for polyanhydrides and is described, for example, in WO 93/21906 to Brown University Research Foundation. In this method, the substance to be incorporated is dispersed or dissolved in a solution of the selected polymer in a volatile organic solvent, such as methylene chloride. This mixture is suspended by stirring in an organic oil, such as silicon oil, to form an emulsion. Microspheres that range between 1-300 microns can be obtained by this procedure. Substances which can be incorporated in the microspheres include pharmaceuticals, pesticides, nutrients, imaging agents, and metal compounds.

5. Coacervation

Encapsulation procedures for various substances using coacervation techniques are known in the art, for example, in GB-B-929 406; GB-B-929 40 1; and U.S. Pat. Nos. 3,266,987, 4,794,000, and 4,460,563. Coacervation involves the separation of a macromolecular solution into two immiscible liquid phases. One phase is a dense coacervate phase, which contains a high concentration of the polymer encapsulant (and optionally one or more active agents), while the second phase contains a low concentration of the polymer. Within the dense coacervate phase, the polymer encapsulant forms nanoscale or microscale droplets. Coacervation may be induced by a temperature change, addition of a non-solvent or addition of a micro-salt (simple coacervation), or by the addition of another polymer thereby forming an interpolymer complex (complex coacervation).

6. Low Temperature Casting of Microspheres

Methods for very low temperature casting of controlled release microspheres are described in U.S. Pat. No. 5,019,400 to Gombotz et al. In this method, a polymer is dissolved in a solvent optionally with one or more dissolved or dispersed active agents. The mixture is then atomized into a vessel containing a liquid non-solvent at a temperature below the freezing point of the polymer-substance solution which freezes the polymer droplets. As the droplets and non-solvent for the polymer are warmed, the solvent in the droplets thaws and is extracted into the non-solvent, resulting in the hardening of the microspheres.

7. Phase Inversion Nanoencapsulation (PIN)

Nanoparticles can also be formed using the phase inversion nanoencapsulation (PIN) method, wherein a polymer is dissolved in a "good" solvent, fine particles of a substance to be incorporated, such as a drug, are mixed or dissolved in the polymer solution, and the mixture is poured into a strong non-solvent for the polymer, to spontaneously produce, under favorable conditions, polymeric microspheres, wherein the polymer is either coated with the particles or the particles are dispersed in the polymer. See, e.g., U.S. Pat.

No. 6,143,211 to Mathiowitz, et al. The method can be used to produce monodisperse populations of nanoparticles and microparticles in a wide range of sizes, including, for example, about 100 nanometers to about 10 microns.

Advantageously, an emulsion need not be formed prior to precipitation. The process can be used to form microspheres from thermoplastic polymers.

8. Sequential Phase Inversion Nanoencapsulation (sPIN)

Multi-walled nanoparticles can also be formed by a process referred to herein as "sequential phase inversion nanoencapsulation" (sPIN). sPIN is particularly suited for forming monodisperse populations of nanoparticles, avoiding the need for an additional separations step to achieve a monodisperse population of nanoparticles.

In sPIN, a core polymer is dissolved in a first solvent. The active agent is dissolved or dispersed in a core polymer solvent. The core polymer, core polymer solvent, and agent to be encapsulated form a mixture having a continuous phase, in which the core polymer solvent is the continuous phase. The shell polymer is dissolved in a shell polymer solvent, which is a non-solvent for the core polymer. The solutions of the core polymer and shell polymer are mixed together. The resulting decreases the solubility of the core polymer at its cloud point due to the presence of the shell polymer solvent results in the preferential phase separation of the core polymer and, optionally, encapsulation of the agent. When a non-solvent for the core polymer and the shell polymer is added to this unstable mixture, the shell polymer engulfs the core polymer as phase inversion is completed to form a double-walled nanoparticle.

sPIN provides a one-step procedure for the preparation of multi-walled particles, such as double-walled nanoparticles, which is nearly instantaneous, and does not require emulsification of the solvent. Methods for forming multi-walled particles are disclosed in U.S. Publication No. 2012-0009267 to Cho, et al. The disclosure of which is incorporated herein by reference.

The particle can be a dendrimer particle. Dendrimers are three-dimensional polymers that are grown by the successive addition of shells or layers of branched molecules to a central core. Dendrimers have several advantages over linear polymers, since they have controllable structure, a single molecular weight rather than a distribution of molecular weights, and a large number of controllable surface functionalities, and an inclination to adopt a globular conformation once a certain size is reached. They are prepared by reacting highly branched monomers together to produce monodisperse, tree-like and/or generational structure polymeric structures. Individual dendrimers consist of a central core molecule, with a dendritic wedge attached to each functional site. The dendrimeric surface layer can have a variety of functional groups disposed thereon, according to the assembly monomers used during the preparation. Generally, the dendrimer functional groups dictate the properties of the individual dendrimer types. As a result of their design, dendrimer cores are spacious, and by modifying the chemical properties of the core, shells, and especially the surface layer, their physical properties can be finely tuned. Tunable properties include solubility, toxicity, immunogenicity and bioattachment capability.

Polyamidoamine, polypropyleneimine, polyarylether and polyethyleneimine are examples of dendrimers that have been investigated for biopharmaceutical applications. Polyamidoamine dendrimers are based on an ethylenediamine core and an amidoamine repeat branching structure. They can be synthesized in a variety of well-defined molecular weights. Their size and surface functionality (primary amine) is defined by the number of controlled repetitive additions of monomeric units, giving rise to different half or full generations. They are water-soluble and they have been reported to be the only class of dendrimer that are monodispersed. Furthermore, they show high charge densities that are restricted to the surface of the molecules.

Dendrimers have been used as carriers for therapeutic compounds, either by entrapment of a drug in cavities within the dendrimer, or by covalently linking drug molecules to the surface. This is reviewed in Svenson, S., Eur J Pharm Biopharm (2009) 71:445-462 and Cheng, Y., J. Pharm. Sci. (2007) 97:123-143. Entrapment within dendrimer cavities is limited to small molecules, and covalent attachment approaches have thus far been limited to systems in which a small drug is hydrolytically or enzymatically cleaved from the dendrimer surface.

Inorganic Particle

Generally, an inorganic particle can have an inorganic content that is at least 50%, 55%, 60%, 65%, 70%, 75%, 80%, 85%, 90% or 95% by mass of the total particle. Exemplary inorganic materials include, for example, at least one type of poorly water-soluble inorganic material from among anhydrides and hydrates of phosphates, silicates, oxides and hydroxides. Of these, preferred use can be made of at least one from among the following: magnesium oxide, magnesium hydroxide, magnesium carbonate, dibasic calcium phosphate, silicon dioxide, aluminum hydroxide, calcium carbonate calcium silicate and aluminum silicate. The inorganic particle can be a ceramic material, hydroxyapatite, or bioactive glass.

Lipid Particle

Drug delivery matrix particles can also be made from a lipid material. Lipids are differentiated compounds in which one portion of the molecule is hydrophobic while another portion is hydrophilic. Suitable lipid materials include phosphatidylethanolamines, such as dioleoylphosphatidylethanolamine, dimyristooylphosphatidylethanolamine, or dipalmitoylphophatidylethanolamine, phosphatidylcholine, phosphatidylglycerol, phosphatidylserine, phosphatidylethanolamine, phosphatidylinositol, sphingomyelin, ganglioside, lysoPC, PEG-lipids, and mixtures thereof.

The original liposome preparation of Bangham et al. (J. Mol. Biol., 1965, 13:238-252) involves suspending phospholipids in an organic solvent, which is then evaporated to dryness leaving a phospholipid film on the reaction vessel. Next, an appropriate amount of aqueous phase is added, the mixture is allowed to "swell", and the resulting liposomes which consist of multilamellar vesicles (MLVs) are dispersed by mechanical means. This preparation provides the basis for the development of the small sonicated unilamellar vesicles described by Papahadjopoulos et al. (Biochim. Biophys, Acta., 1967, 135:624-638), and large unilamellar vesicles.

Techniques for producing large unilamellar vesicles (LUVs), such as, reverse phase evaporation, infusion procedures, and detergent dilution, can be used to produce liposomes. A review of these and other methods for producing liposomes may be found in the text Liposomes, Marc Ostro, ed., Marcel Dekker, Inc., New York, 1983, Chapter 1, the pertinent portions of which are incorporated herein by reference. See also Szoka, Jr. et al., (1980, Ann. Rev. Biophys. Bioeng., 9:467), the pertinent portions of which are also incorporated herein by reference.

Other techniques that are used to prepare vesicles include those that form reverse-phase evaporation vesicles (REV), Papahadjopoulos et al., U.S. Pat. No. 4,235,871. Another class of liposomes that may be used is characterized as having substantially equal lamellar solute distribution. This class of liposomes is denominated as stable plurilamellar vesicles (SPLV) as defined in U.S. Pat. No. 4,522,803 to Lenk, et al. and includes monophasic vesicles as described in U.S. Pat. No. 4,588,578 to Fountain, et al. and frozen and thawed multilamellar vesicles (FATMLV) as described above.

A variety of sterols and their water soluble derivatives such as cholesterol hemisuccinate have been used to form liposomes; see specifically Janoff et al., U.S. Pat. No. 4,721,612, issued Jan. 26, 1988, entitled "Steroidal Liposomes." Mayhew et al., PCT Publication No. WO 85/00968, published Mar. 14, 1985, described a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., PCT Publication No. 87/02219, published Apr. 23, 1987, entitled "Alpha Tocopherol-Based Vesicles".

In a liposome-drug delivery system, a bioactive agent such as a drug is entrapped in the liposome and then administered to the patient to be treated. For example, see Rahman et al., U.S. Pat. No. 3,993,754; Sears, U.S. Pat. No. 4,145,410; Paphadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578. Alternatively, if the bioactive agent is lipophilic, it may associate with the lipid bilayer.

The lipid based particle can also be in a non-liposomal form. It is typically easier to incorporate hydrophobic drugs into a non-liposomal lipid particle than a particle in the liposomal form. Such non-liposomal lipid complexes are characterized, for example, by: (1) freeze-fracture electron micrographs (Deamer et al., Biochim. Biophys. Acta, 1970, 219:47-60), demonstrating non-liposomal complexes; (2) captured volume measurements (Deamer et al., Chem. Phys. Lipids, 1986, 40:167-188), demonstrating essentially zero entrapped volumes and therefore being non-liposomal; (3) differential scanning calorimetry (DSC) (Chapman, D., in: Liposome Technology, Gregoriadis, G., ed., 1984, CRC Press, Boca Raton), showing no lipid bilayer pretransition phase or main transition; (4) 31P-NMR spectra (Cullis et al., 1982 in: Membrane Fluidity in Biology, Academic Press, Inc., London & N.Y.), suggesting characteristics of highly immobilized lipid (broad isotropic); and (5) x-ray diffraction data (Shipley et al., in: Biomembranes, 1973, Chapman, D. and Wallach, D., eds., Vol 2: 1, Academic Press, Inc., London & N.Y.), indicative of gel phase lipid. Also characteristic of these systems is the complete association of the drug with the lipid as evidenced by density gradient centrifugation. In this technique the gradient is centrifuged at an elevated force (about 230,000×g) for about 24 hours. This insures that all the components in the gradient reach their equilibrium density positions. Elution profiles of these systems show overlapping drug and lipid peaks, which indicates all of the drug is associated with the lipid.

Outer Shell Platelet Membrane

The outer shell platelet membrane can be a natural or synthetic membrane comprising platelet proteins capable of interacting with cancer cells. In some cases, the platelet membrane is produced by lysing platelets, such as autologous platelets from the subject to be treated. In other cases, the outer shell is a synthetic membrane, such as a liposome, engineered to contain platelet proteins capable of interacting with cancer cells. For example, the outer shell platelet membrane can comprise P-selectin protein. The shell platelet membrane can comprise integrin $\alpha_{IIb}\beta_3$. The shell platelet membrane can comprise a self-recognized immunomodulatory protein selected from the group consisting of CD47, CD55, and CD59.

Heterologous Extracellularly Active Proteins

Whether natural or synthetic, the outer shell platelet membrane can be engineered to include at least one heterologous extracellularly active protein. This extracellularly active protein can be any protein, natural or synthetic, that will have a therapeutic effect when in contact with a cancer cell. For example, the extracellularly active protein can be a tumor necrosis factor (TNF)-related apoptosis inducing ligand (TRAIL), which can bind the DR4 and DR5 death receptors on tumor cells and induce apoptosis. As another example, the extracellularly active protein can be a therapeutic antibody, such as cetuximab, trastuzumab, or a combination thereof.

Intracellularly Active Drugs

The drug delivery matrix can be used to encapsulate an intracellularly active drug that is released from the inner core inside a targeted cell. This drug can be any type of molecule with a therapeutic activity inside a cell, such as a protein, nucleic acid (miRNA, RNAi, dsDNA, etc. . . . ), or small molecule compound. The drug delivery matrix can be selected based on the desired intracellularly active drug to be encapsulated. Therefore, the intracellularly active drug can be either hydrophilic or hydrophobic.

Drugs to Treat Cancer

In some embodiments, the intracellularly active drug is a hydrophilic or hydrophobic anti-neoplastic drug. For example, the drug can be selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Akynzeo (Netupitant and Palonosetron Hydrochloride), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, Carmubris (Carmustine), Carmustine, Carmustine Implant, Casodex (Bicalutamide), CeeNU (Lomustine), Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRICETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINECISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Interferon Alfa-2b, Recombinant, Intron A (Recombinant Interferon Alfa-2b), Iodine I 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Netupitant and Palonosetron Hydrochloride, Neupogen (Filgrastim), Nexavar (Sorafenib Tosylate), Nilotinib, Nivolumab, Nolvadex (Tamoxifen Citrate), Nplate (Romiplostim), Obinutuzumab, Odomzo (Sonidegib), OEPA, Ofatumumab, OFF, Olaparib, Omacetaxine Mepesuccinate, Oncaspar (Pegaspargase), Ondansetron Hydrochloride, Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, Pegaspargase, Peginterferon Alfa-2b, PEGIntron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and Iodine I 131 Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Unituxin (Dinutuximab), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

Drugs to Treat Vascular Disease

In some embodiments, the disclosed nanovehicle can be targeted to damaged vascular endothelium for site-selective delivery of a therapeutic for coagulation or coronary restenosis. For example, in some cases, the intracellularly active drug can be selected from the group consisting of Adcirca (tadalafil), Adempas (riociguat), Agrylin (anagrelide HCL), Angiomax (bivalirudin), Atacand (candesartan cilexetil), Atryn (antithrombin recombinant lyophilized powder for reconstitution), Azor (amlodipine besylate; olmesartan medoxomil), Baycol (cerivastatin sodium), BiDil (isosorbide dinitrate/hydralazine hydrochloride), Brilinta (ticagrelor), Caduet (amlodipine/atorvastatin), Captopril, Cardizem® (Diltiazem HC1 for injection) Monvial®, CellCept, Cleviprex (clevidipine), Corlanor (ivabradine), Corlopam, Corvert Injection (ibutilide fumarate injection), Covera-HS (verapamil), Crestor (rosuvastatin calcium), Diltiazem HCL, Diovan (valsartan), Doxorubicin, DynaCirc CR, Edarbi (azilsartan medoxomil), Edarbyclor (azilsartan medoxomil and chlorthalidone), Efient (prasugrel), Eliquis (apixaban), Entresto (sacubitril and valsartan), Epanova (omega-3-carboxylic acids), Fenofibrate, Heparin, Innohep (tinzaparin sodium) injectable, Integrilin, Juxtapid (lomitapide), Kengreal (cangrelor), Kynamro (mipomersen sodium), Lescol (fluvastatin sodium), Lescol (fluvastatin sodium) capsules, Rx, Letairis (ambrisentan), Levitra (vardenafil), Lexxel (enalapril maleatefelodipine ER), Lipitor (atorvastatin calcium), Liptruzet (ezetimibe and atorvastatin), Livalo (pitavastatin), Mavik (trandolapril), Micardis (telmisartan), Micardis HCT (telmisartan and hydrochlorothiazide), Microzide (hydrochlorothiazide), Multaq (dronedarone), Natrecor (nesiritide), Niaspan, Normiflo, Nymalize (nimodipine), Opsumit (macitentan), Pentoxifylline, Pindolol, Plavix (clopidogrel bisulfate), Plavix (clopidogrel bisulfate), Posicor, Pradaxa (dabigatran etexilate mesylate), Pravachol (pravastatin sodium), Pravachol (pravastatin sodium), Prestalia (perindopril arginine and amlodipine besylate), Prinivil or Zestril (Lisinopril), ProAmatine (midodrine), Ranexa (ranolazine), Remodulin (treprostinil), ReoPro, REPRONEX(menotropins for injection, USP), Retavase (reteplase), Rythmol, Savaysa (edoxaban), Soliris (eculizumab), Teczem (enalapril maleate/diltiazem malate), Tekamlo (aliskiren+amlodipine), Tekturna (aliskiren), Teveten (eprosartan mesylate plus hydrochlorothiazide), Teveten (eprosartan mesylate), Tiazac (diltiazem hydrochloride), Tiazac (diltiazem hydrochloride), Tiazac (diltiazem hydrochloride), Toprol-XL (metoprolol succinate), Tribenzor (olmesartan medoxomil+amlodipine+hydrochlorothiazide), Tricor (fenofibrate), Trilipix (fenofibric acid), Tyvaso (treprostinil), Varithena (polidocanol injectable foam), Vascepa (icosapent ethyl), Visipaque (iodixanol), Xarelto (rivaroxaban), Xarelto (rivaroxaban), Zocor, Zontivity (vorapaxar)

Pharmaceutical Compositions

Disclosed is a pharmaceutical compositions containing therapeutically effective amounts of one or more of the disclosed nanovehicles and a pharmaceutically acceptable carrier. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. For example, the compounds may be formulated or combined with known NSAIDs, anti-inflammatory compounds, steroids, and/or antibiotics.

Methods

Also disclosed is a method for treating cancer in a subject that involves administering to the subject a platelet membrane-coated nanovehicle disclosed herein. In some cases, the platelet membrane is autologous, i.e., produced from a platelet obtained from the subject.

In some cases, the method can be used to treat any cancer that overexpresses CD44. Therefore, in some cases, the method further involves assaying a sample from the subject for CD44 expression, and treating the subject with the disclosed platelet membrane-coated nanovehicle if elevated CD44 levels are detected.

The cancer may be a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. In certain embodiments, the cancer is ovarian cancer. In particular aspects, the cancer may be a chemo-resistant cancer. In some cases, the cancer is a circulating cancer cell.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Also disclosed is a method for treating vascular disease in a subject that involves administering to the subject a platelet membrane-coated nanovehicle disclosed herein. In these embodiments, the drug delivery matrix encapsulates a drug to treat vascular disease, e.g., coagulation or coronary restenosis. For example, the drug can be heparin or doxorubicin.

Administration

The disclosed pharmaceutical compositions may be administered intravenously, intradermally, intraarterially, intraperitoneally, intralesionally, intracranially, intraarticularly, intraprostaticaly, intrapleurally, intratracheally, intravitreally, intravaginally, intrarectally, intratumorally, intramuscularly, intraperitoneally, subcutaneously, subconjunctival, intravesicularlly, mucosally, intrapericardially, intraumbilically, intraocularally, intrathecally, locally, by injection, by infusion, by continuous infusion, by localized perfusion bathing target cells directly, via a catheter, or via a lavage. For example, the composition may be administered by injection or infusion.

In some embodiments, the pharmaceutical compositions are administered parenterally by injecting the composition close to the site of a tumor. As used herein, "close to the site of a tumor" is meant to refer to local targeting and delivery of the composition to the site of the tumor and is meant to include direct injection into the tumor as well as injection within about 1 cm (e.g., within 1 cm, within about 5 mm, within 5 mm, within about 2 mm, within 2 mm, etc.) of the tumor. The pharmaceutical composition can be administered, for example, via a single injection or via multiple injections, such as in the case where the pharmaceutical composition is administered by injecting it both into the tumor and around the periphery of the tumor. In some embodiments, pharmaceutical compositions are administered systemically to the subject, for example, as in the case where the pharmaceutical compositions are administered intravenously, such as by injecting the composition into the subject's circulatory system. In some embodiments, the pharmaceutical compositions are administered enterally, for example, to irrigate a tumor in the gastrointestinal tract.

To have a better therapeutic benefit, the composition may be administered in combination with at least an additional agent selected from the group consisting of a radiotherapeutic agent, a hormonal therapy agent, an immunotherapeutic agent, a chemotherapeutic agent, a cryotherapeutic agent and a gene therapy agent.

For a safe and effective dosage, the composition may be administered at a dose of about 1 to about 200 mg/kg body weight, about 1 to about 100 mg/kg body weight, 1 to about 50 mg/kg body weight, about 1 to about 20 mg/kg body weight, about 3 to about 10 mg/kg body weight, about 3 to about 6 mg/kg body weight or any range derivable therein to a subject.

Kits

Also disclosed is a kit for producing the disclosed nanovehicles. As the nanovehicles can be produced from autologous platelets, the kit can comprise reagents for extracting platelet membranes from a blood sample from the subject. Examples of suitable reagents include a lysis buffer, ACD Buffer (Acid-Citrate-Dextrose), CPD Buffer (Citrate-Phosphate-Dextrose), Platelet Wash Buffer (10 mM sodium citrate, 150 mM NaCl, 1 mM EDTA, 1% (w/v) dextrose, pH 7.4), HEPES Buffer, Tyrode's Buffer, PBS Buffer, or any combination thereof. The kit can further contain drug-loaded inner core particles. Alternatively, the kit can contain reagents for producing these particles. The kit can further contain reagents for coating the inner core particles with platelet membrane isolated from the subject. Examples of suitable reagents include glycerol dimethacrylate, anionic sodium 1,4-bis-2-ethylhexylsulfosuccinate (AOT), poly (ethyleneglycol) dodecyl ether (Brij-30), ammonium persulfate solution, tetramethylethylenediamine (TMEDA), Traut's reagent, sulfosuccinimidyl-4-(N-maleimidomethyl) cyclohexane-1-carboxylate (Sulfo-SMCC) solution, ethanol, or any combination thereof.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Anticancer Platelet Membrane-coated Nanovehicles

Methods

Isolation of platelets. Platelets from whole blood were isolated through gradient centrifugation (Donovan L E, et al. (2013) Alzheimers Res Ther 5(32):10.1186). Briefly, 10 mL whole mouse blood was centrifuged at 100×g for 20 min with no brake. Afterward, the supernatant was added with PGE1 to a final concentration of 1 µM and centrifuged at 800×g for 20 min. The platelets was washed by the citrate buffer and centrifuged repeatedly. To assess the purity of the isolated platelets, flow cytometry was performed after double labeling with antibodies against the platelet-specific marker, CD41 and a marker for white blood cells, CD45.

Preparation of PM-NV. The NV encapsulated with Dox was prepared using a single emulsion method. Briefly, 500 µL aqueous phase containing 46 mg acrylamide (AAm), 2 mg N-(3-aminopropyl) methacrylamide (APMAAm) and 16 mg glycerol dimethacrylate (GDA) was added into the organic phase containing a mixture of hexane (5 mL) and two surfactants: anionic sodium 1,4-bis-2-ethylhexylsulfosuccinate (AOT, 178 mg), poly(ethyleneglycol) dodecyl ether (Brij-30, 344 mg) and ammonium persulfate (APS). After stirred for 10 min, the mixture was added with tetramethylethylenediamine (TMEDA) for initiation of polymerization and maintained for 2 h. Then the NV was precipitated and washed by ethanol after evaporating hexane. Nondegradable NV was made by replacing the degradable crosslinker GDA with nondegradable N,N'-methylene-bis acrylamide (MBA).

To acquire purified platelets membrane, the obtained platelets were added into lysis buffer and maintained for 30 min. Thereafter, the mixture was centrifuged at 18,000×g for 10 min. After sonication, the obtained PM and Dox-NV mixture was stirred and maintained overnight. To decorated TRAIL on the surface of PM, PM was first reacted with Traut's reagent to generate additional thiol groups, which was further linked with amines of TRAIL through the sulfosuccinimidyl-4-(Nmaleimidomethyl) cyclohexane-1-carboxylate (Sulfo-SMCC). To access the amount of TRAIL on the PM, TRAIL was reacted with FITC-NHS or Cy5.5-NHS overnight and purified by using G-25 column (PD midiTRAP™, GE Healthcare). The amount of TRAIL was determined by measuring the fluorescence intensity of FITC/Cy5.5 via microplate reader (Infinite M200 PRO, Tecan). The TRAILDox-PM-NV was characterized by the Zetasizer (Nano ZS, Malvern) and Transmission Electron Microscopy (TEM) (JEM-2000FX, Hitachi) operating at 200 kV.

In vitro stability of PMNNV and Dox release from PM-NV. For in vitro stability of PM-NV, PM-NV and NV were added into 100% FBS (Hyclone). Absorbance measurements at 560 nm were taken at pre-determined time intervals using a microplate reader. For in vitro Dox release, 0.5 mL of Dox-PMNV and Dox-NV was added into a dialysis tube (10K MWCO) (Slide-A-Lyzer, Thermo Scientific) embedded into 14 mL of the PBS buffer solution (containing 0.1% Tween-80) at different pH, and gently shaken at 37° C. in a shaker (New Brunswick Scientific) at 100 rpm. At predetermined time intervals, the total buffer solution was withdrawn, followed by replacing with 14 mL of fresh buffer solution with the same pH. The fluorescence intensity of Dox released was measured at 596 nm with an excitation wavelength of 480 nm by a microplate reader.

Cell culture. MDA-MB-231 cells and Raw 264.7 were obtained from Tissue Culture Facility of UNC Lineberger Comprehensive Cancer Center and cultured in Dulbecco's Modified Eagle Medium (DMEM) with 10% (v:v) FBS, 100 U/mL penicillin and 100 µg/mL streptomycin.

Site-specific delivery of TRAIL and Dox. MDA-MB-231 cells ($1 \times 10^5$ cells/well) were seeded in a confocal microscopy dish (MatTek). After culture for 24 h, the cells were incubated with TRAIL-PMNV and TRAIL-NV for 2 h. Thereafter, the cells were washed with PBS and stained with Alexa Fluor 488-labeled wheat germ agglutinin (WGA) for 10 min. After washing with PBS twice, the cells were immediately subjected to CLSM (LSM 710, Zeiss) for observation. For intracellular Dox observation, MDA-MB-231 cells were seeded in a confocal microscopy dish at the density of $1 \times 10^5$ cells/well. Twenty-four hours later, the cells were exposed to Dox-PM-NV. After incubation for 1 h and 4 h, the cells were washed with PBS, stained with lysosome tracker and Hoechst, and observed by CLSM.

In vivo targeting capability of PM-NV. All animals were treated in accordance with the Guide for Care and Use of Laboratory Animals, approved by the Institutional Animal Care and Use Committee (IACUC) of University of North Carolina at Chapel Hill and North Carolina State University. To build MDA-MB-231 tumor-bearing mice model, the female nude mice (6 weeks, J:NU, The Jackson Laboratory) were subcutaneously implanted with $1 \times 10^7$ MDA-MB-231 cells in 100 µL saline. When the volume of tumors reached to 400-600 mm$_3$, the mice were intravenously injected with Cy5.5-labeled TRAIL-Dox-NV and Cy5.5-labeled TRAIL-Dox-PM-NV at Cy5.5 dose of 20 nmol/kg. Images of mice were taken on IVIS Lumina imaging system (Caliper, USA) at 6, 12, 24 and 48 h post injection. Thereafter, the mice were euthanized at 48 h post injection. The tumors and major organs (heart, liver, spleen, lung, kidney) were harvested and subjected for ex vivo imaging. The fluorescence intensities of region-of interests (ROI) were analysed by Living Image Software. For Dox distribution at tumor site, Dox-NV and Dox-PM-NV were intravenously injected into MDA-MB-231 tumor-bearing mice via tail vein at the Dox dose of 2 mg/kg. Then mice were euthanized and tumors were taken out for frozen section at 3 h post injection. Hoechst 33342 was used for nuclear staining. The stained tumor slides were observed by fluorescence microscope.

In vivo antitumor efficacy assay. Twenty-five tumor-bearing mice were weighed and randomly divided into five groups (n=5) when the tumor volume reached to 60 mm$^3$. From day 0, the mice were intravenously injected with TRAIL-Dox-NV (TRAIL: 1 mg/kg, Dox: 2 mg/kg), TRAIL-PM-NV, Dox-PM-NV, TRAIL-Dox-PM-NV and saline as a control every other day for 12 days. The tumor size and body weight were measured every two days. At day 16, the tumors and the organs were collected, washed with PBS thrice and fixed for further section. For the hematoxylin and eosin (H&E) staining, the slides of tumors and organs were observed by optical microscope (DM5500B, Leica). For the TUNEL apoptosis assay, the fixed tumor sections were stained by the In Situ Cell Death Detection Kit (Roche Applied Science) according to the manufacturer's protocol and observed by fluorescence microscope.

In vivo elimination of CTCs. Mice were anesthetized using isoflurane and followed by the intravenous injection of saline, TRAIL-Dox-NV and TRAIL-Dox-PM-NV at TRAIL concentration of 15 µg/mL via tail vein. Thirty minutes later, the mice were intravenously injected with $1 \times 10^7$ MDA-MB-231 cells in 100 µL saline via tail vein. Thereafter, the lung tissues of mice were stained with India ink and taken out for imaging and staining at 8 weeks post injection. For the hematoxylin and eosin staining, the slides of lungs were observed by optical microscope.

Materials. All chemicals were purchased from Sigma-Aldrich and were used as received. Fluorescein isothiocyanate (FITC)-NHS, rhodamine-NHS and Cy5.5-NHS were purchased from Life Technologies (Grand Island, N.Y., USA). Glycerol dimethacrylate was purchased from Tokyo Chemical Industry Co., Ltd. (Tokyo, Japan).

Determination of endocytosis pathways. MDA-MB-231 cells ($1 \times 10^5$ cells/per well) were seeded in the 6-well plates and cultured for 24 h. In order to investigate the endocytosis pathway, the cells were pre-incubated with various kinds of endocytosis inhibitor, including clathrin-mediated endocytosis: sucrose (SUC, 450 mM) (Mo R, et al. (2012) Advanced Materials 24(27):3659-3665) and chlorpromazine (CPZ, 10 µM) (Zhang X-X, et al. (2011) Molecular pharmaceutics 8(3):758-766); inhibitor of caveolin-mediated endocytosis: nystatin (NYS, 25 µg/mL) (ur Rehman Z, et al. (2011) Journal of Controlled Release 156(1):76-84); inhibitor of micropinocytosis: amiloride (AMI, 1 mM) (Koivusalo M, et al. (2010) The Journal of cell biology 188(4):547-563); inhibitor of lipid raft: methyl-β-cyclodextrin (MCD, 3 mM)

(Chiu Y-L, et al. (2010) Journal of Controlled Release 146(1):152-159) for 1 h at 37° C., respectively. Afterward, the cells were incubated with Dox-PM-NV at the Dox concentration of 200 ng/mL in the presence of inhibitors for additional 2 h. After washing the cells with PBS twice, the fluorescence intensity of Dox in the cells were measured via flow cytometry.

Evaluation of Dox-PM-NG uptake by Raw 264.7 cells. Raw 264.7 cells ($1\times10^5$ cells/per well) were seeded in the 6-well plates and cultured for 24 h. Afterwards, the cells was added with Dox-NV and Dox-PM-NV and incubated for 2 h. Then the cells were washed with PBS and subjected to fluorescence microscopy observation. For quantitative analysis, the cells were subjected to flow cytometry for fluorescence signals quantification.

Apoptosis assay. Apoptosis of MDA-MB-231 cells was detected using the Annexin V-FITC Apoptosis Detection Kit (BD Biosciences) and APO-BrdU TUNEL Assay Kit (Life Technologies), respectively. The cells were seeded in the 6-well plates at the density of $1\times10^5$ cells/well. After culture for 48 h, the cells were incubated with drug-free DMEM, TRAIL-Dox-NV, TRAIL-PM-NV, Dox-PM-NV and TRAIL-Dox-PM-NV for 12 h. The subsequent procedures were performed in accordance with the manufacturer's protocol. For Annexin V-FITC apoptosis detection, the cells were analyzed by flow cytometry (BD FACSCalibur). While for TUNEL assay, the cells were observed by fluorescence microscope (IX71, Olympus).

In vitro cytotoxicity. MDA-MB-231 cells ($5\times10^3$ cells/well) were seeded in the 96-well plates. Twenty-four hours later, the cells were treated with TRAIL-Dox-NV, TRAIL-PM-NV, Dox-PM-NV and TRAIL-Dox-PMNV with different TRAIL/Dox concentrations and incubated for 24 h. Then the cells were added with 20 µL of the MTT solution (5 mg/mL). After 4 h incubation, the medium was replaced with 150 µL of dimethyl sulfoxide (DMSO). The absorbance was measured at the wavelength of 570 nm by a microplate reader.

In vivo pharmacokinetics investigation. In vivo pharmacokinetics of Dox-NV and DoxPM-NV were investigated using Sprague-Dawley (SD) rats (200±20 g). Six SD rats were randomly divided into two groups (n=3). The rats were intravenously injected with Dox-NV and Dox-PM-NV at the Dox dose of 5 mg/kg via the tail vein. At pre-determined time intervals (0.25, 0.5, 1, 3, 6, 12, 24, and 48 h), blood samples were collected and centrifuged at 800 g for 10 min. The supernatant was then analysed by measuring the fluorescence intensity of Dox.

Statistics. All results presented are Mean±s. d. Statistical analysis was performed using Student's t-test. With a p value<0.05, the differences between experimental groups and control groups were considered statistically significant.

Results

Figure 2A:
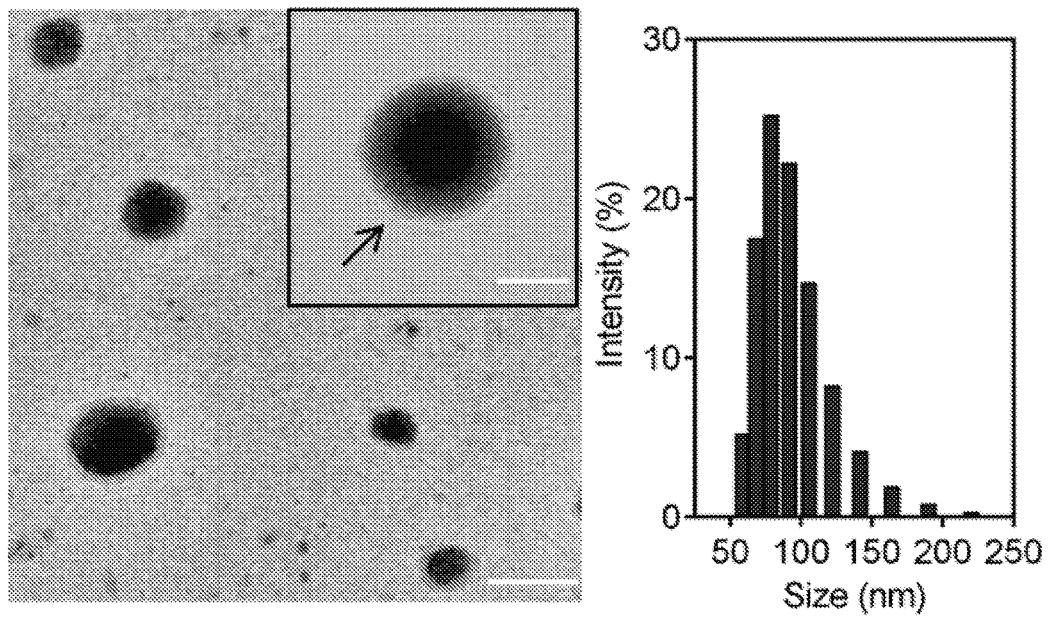
FIGS. 2A to 2D show characterization of PM-NV.
Figure 2B:
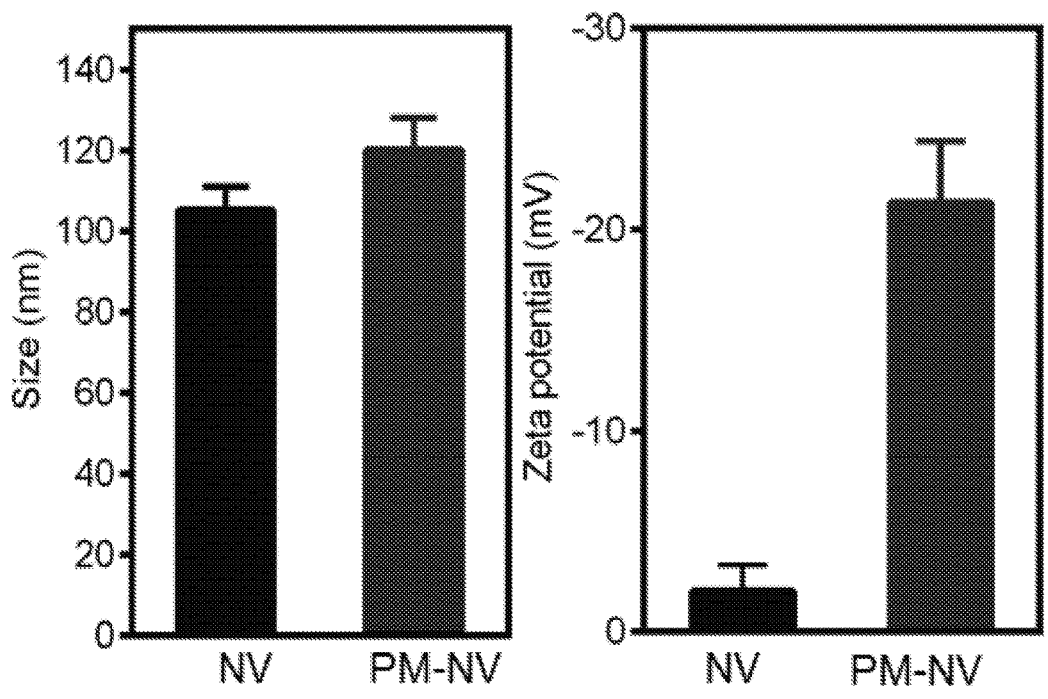
Figure 2C:
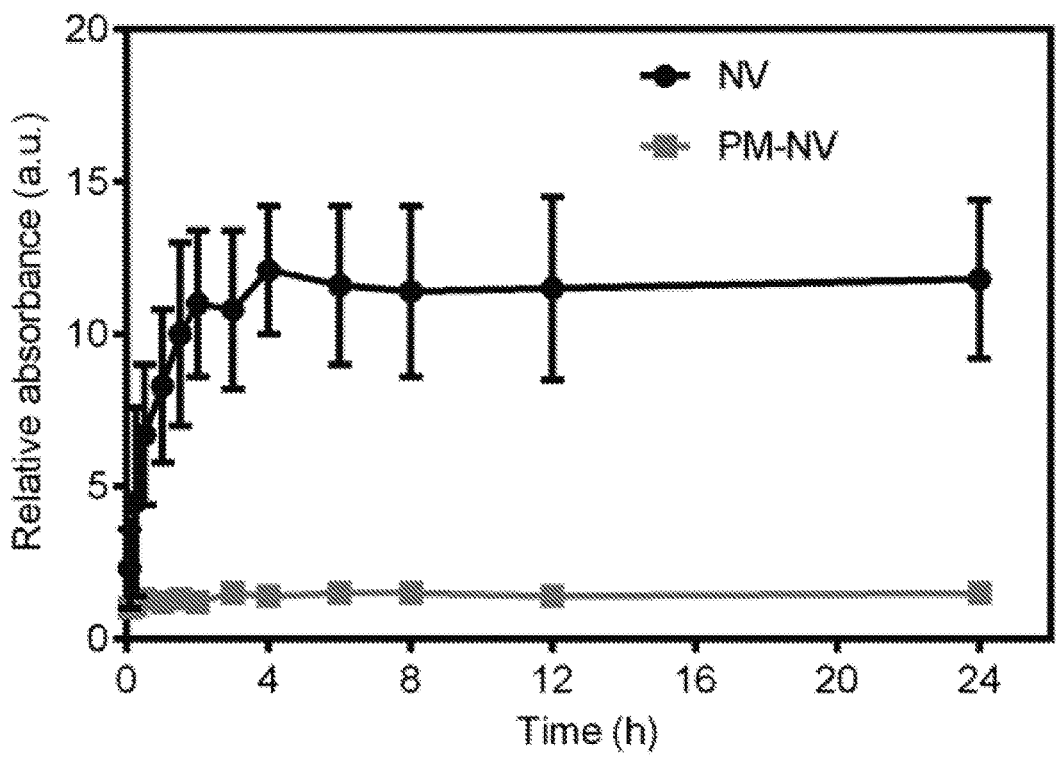
Figure 7:
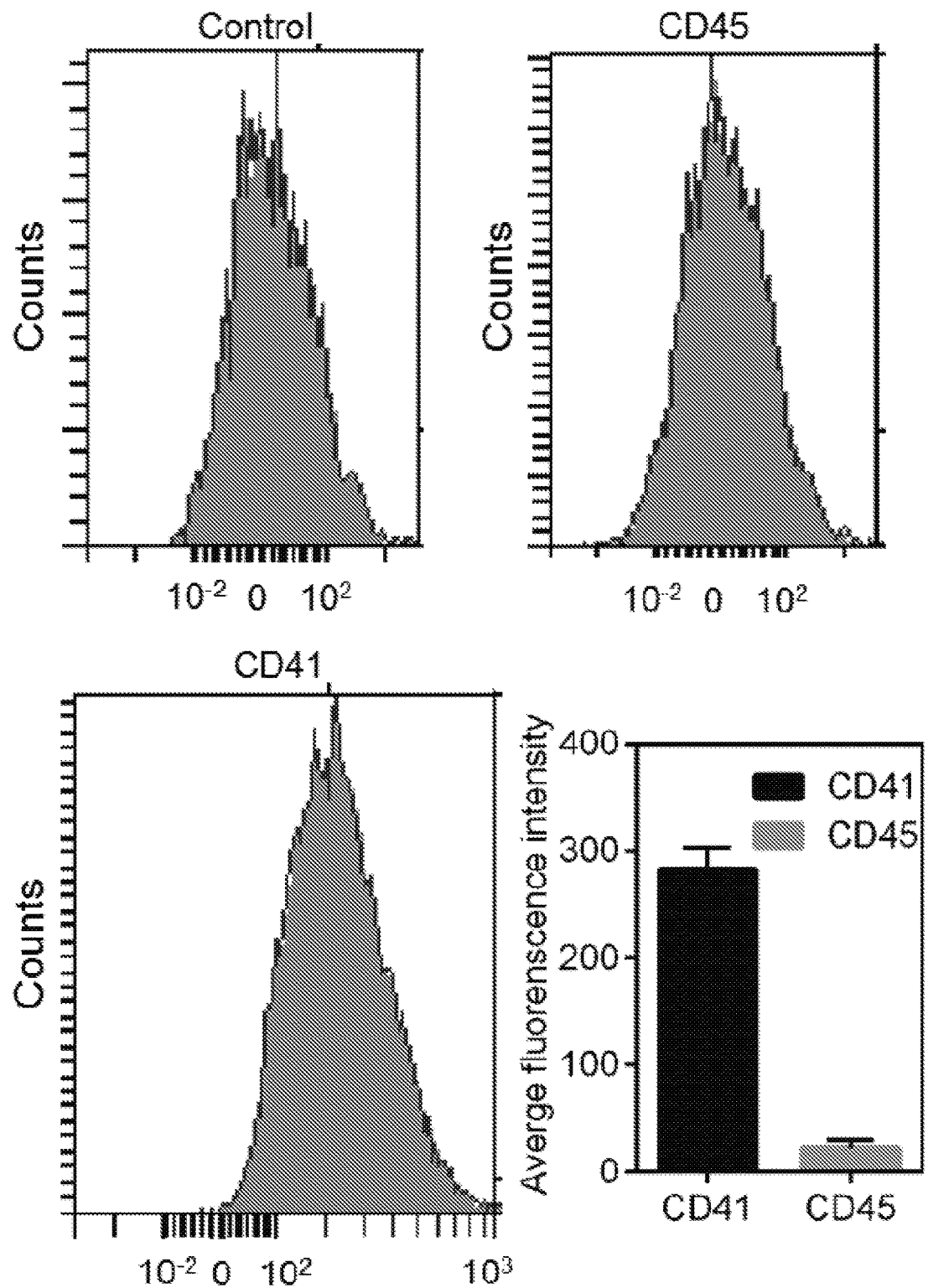
FIG. 7 shows results of FACS study of purified platelets that were double stained for FITC-conjugated, anti-CD45 (white blood cell marker) and anti-CD41 (platelet marker).

Preparation and characterization of platelet membrane-coated nanovehicles (TRAILDox-PM-NV). In order to prepare TRAIL-Dox-PM-NV, the purified platelets were collected through the gradient centrifugation (Qureshi A H, et al. (2009) PLoS One 4(10):e7627; Donovan L E, et al. (2013) Alzheimers Res Ther 5(32):10.1186). The obtained platelets were verified by fluorescence-activated cell sorting (FACS) study through labeling with antibodies against the platelet-specific marker, CD41 (Boilard E, et al. (2010) Science 327(5965):580-583), and a marker for white blood cells (WBC), CD45 (Aicher A, et al. (2003) Nat Med. 9(11):1370-1376). Strong fluorescence signals associated with CD41 were observed and signals associated with CD45 were barely observed (FIG. 7), indicating that the isolated platelets were highly purified and not contaminated by WBC. PM-NV was prepared via coating the purified platelet membranes on the surface of NV. Monodispersed NV was obtained with a particle size of 105 nm and zeta potential of −2.0 mV (FIG. 8), characterized by the dynamic light scattering (DLS). After coating with PM, the resulting PM-NV appeared as a core-shell structure with an average diameter of 120.9 nm and zeta potential of −21.3 mV (FIG. 2A). The increased size and decreased surface charge indicated the existence of PM on the surface of NV (Fang R H, et al. (2014) Nano letters 14(4):2181-2188) (FIG. 2B). Additionally, the successful coating of PM was further confirmed by colocalization of the FITC-labeled PM and rhodamine-labeled NV (FIG. 9). To investigate the stability of PM-NV, the size changes of NV and PM-NV was monitored by the absorbance method (Popielarski S R, et al. (2005) Bioconjug Chem. 16(5):1063-1070; Fang R H, et al. (2010) Langmuir 26(22):16958-16962). The absorbance values measured at 560 nm suggested the superior serum stability of PM-NV when compared with NV (FIG. 2c).

Figure 2D:
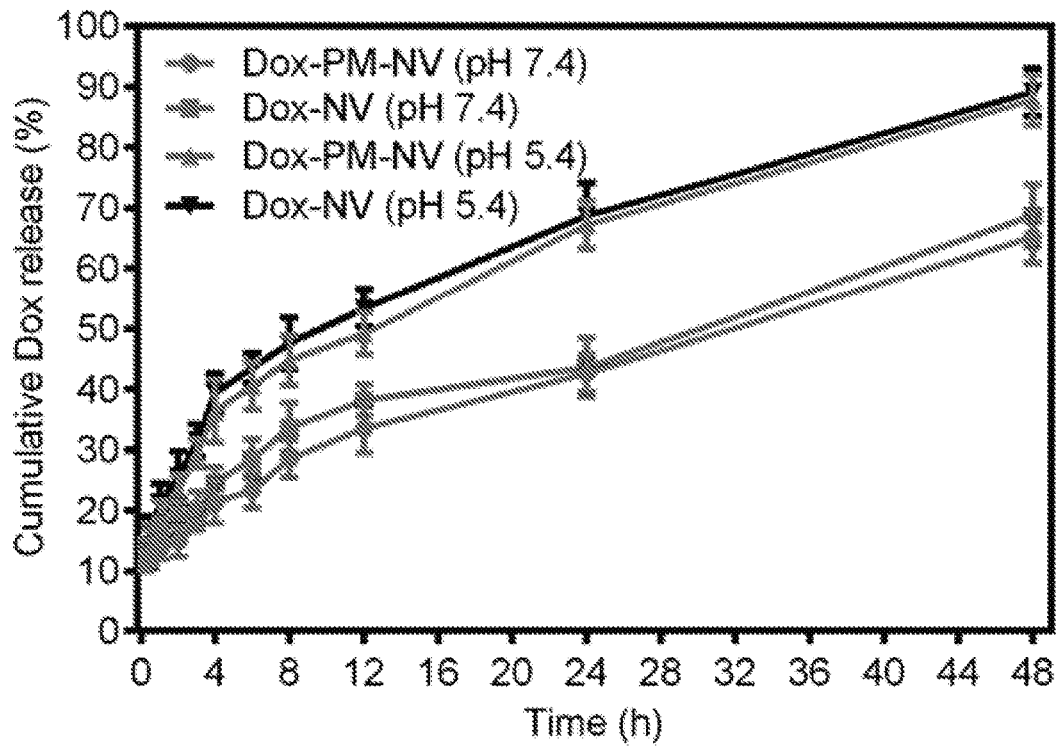

To characterize the pH-responsive release behavior of Dox from PM-NV, a nondegradable crosslinker, methylen-ebis-(acrylamide) (Cohen J A, et al. (2008) Bioconjug Chem. 20(1):111-119) was applied to substitute glycerol dimethacrylate (GDA) to prepare nondegradable NV as a control. The in vitro release profile of Dox from degradable and nondegradable PM-NV was monitored at pH 5.4 and 7.4, respectively. Only about 23% of Dox was released from both degradable and nondegradable PM-NV within 6 h and approximately 65% of Dox was released within 48 h at pH 7.4. In contrast, degradable PM-NV showed much higher cumulative Dox release than nondegradable PM-NV at pH 5.4. More than 40% of TRAIL was released in the first 6 h from degradable PM-NV and about 88% of Dox was released within 48 h (FIG. 2d). Furthermore, it is also noteworthy that the coating of PM could decline the release rate of Dox, suggesting that the PM could inhibit the burst release of drugs from NV. Collectively, it was demonstrated that the acidic environment accelerated the dissociation of PM-NV and subsequent release of encapsulated Dox.

Figure 3A:
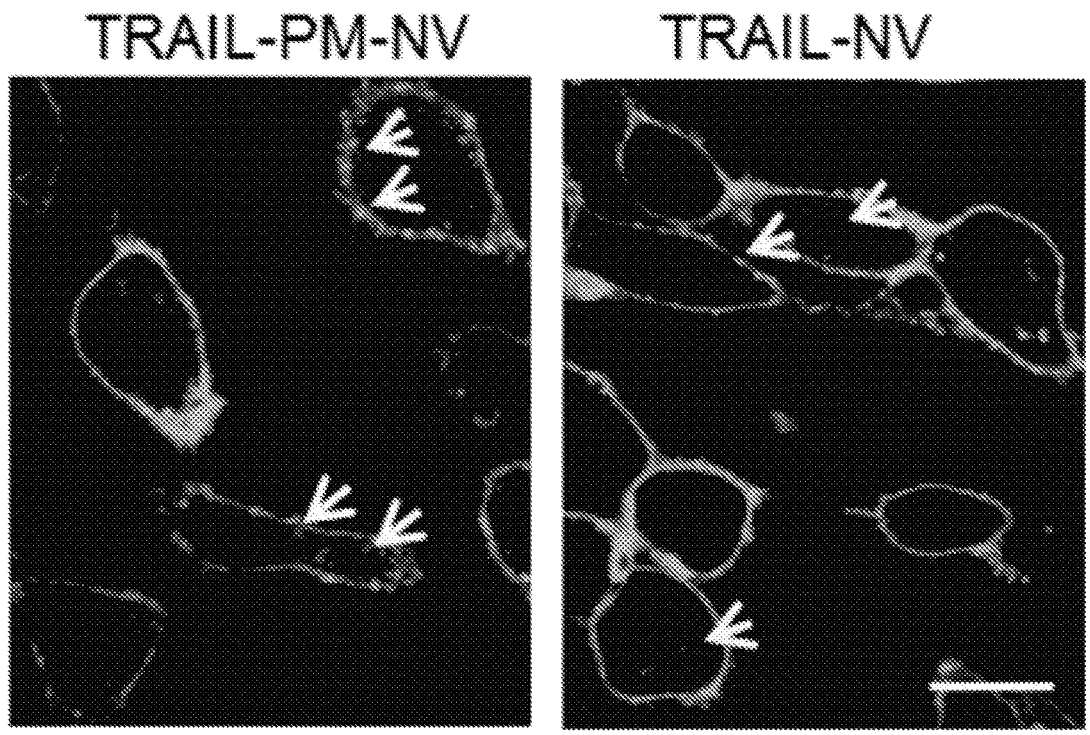
FIGS. 3A to 3E show in vitro site-specific delivery of TRAIL and Dox by PM-NV.

Site-specific Delivery of TRAIL and Dox by PM-NV. To investigate the delivery efficacy of TRAIL and Dox by PM-NV, the human breast adenocarcinoma (MDA-MB-231) cells (Sheridan C, et al. (2006) Breast Cancer Res 8(5):R59) were incubated with NV and PM-NV for 2 h, followed by the observation via confocal laser scanning microscopy (CLSM). An evident difference of distribution of TRAIL delivered by NV and PM-NV was recorded. As displayed in FIG. 3A, the distribution of the rhodamine-labeled PM-NV was located on the cellular membrane and cytoplasm. In contrast, all of the rhodamine-labeled non-coated NV was found in the cytoplasm, indicating directly decorated TRAIL on the surface of NV could be easily transported into the cells. The efficient delivery of TRAIL toward plasma membrane mediated by PM-NV could be attributed to the selective affinity of platelets and cancer cells. The P-Selectin protein overexpressed on the surface of platelets could specifically bind to the CD44, an upregulated receptors on the cancer cell membrane. Collectively, the selective binding interaction between platelets and cancer cells lead to an efficient extracellular delivery of TRAIL, subsequently triggering the following extrinsic apoptosis pathway.

Figure 3B:
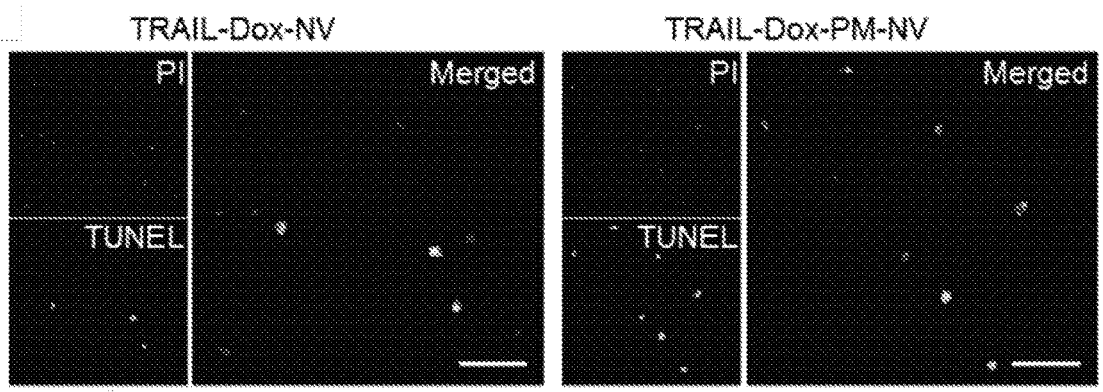
Figure 3C:
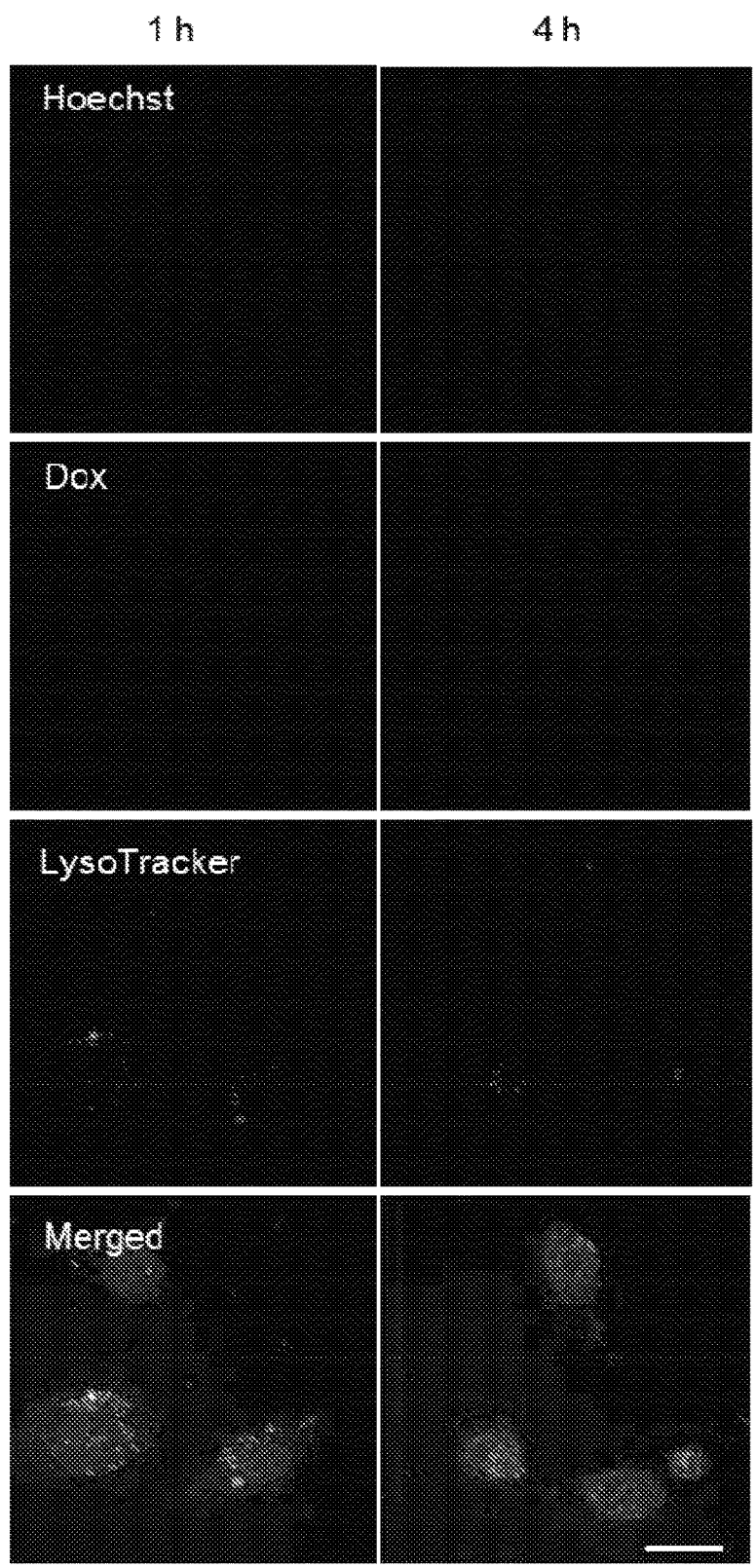
Figure 10:
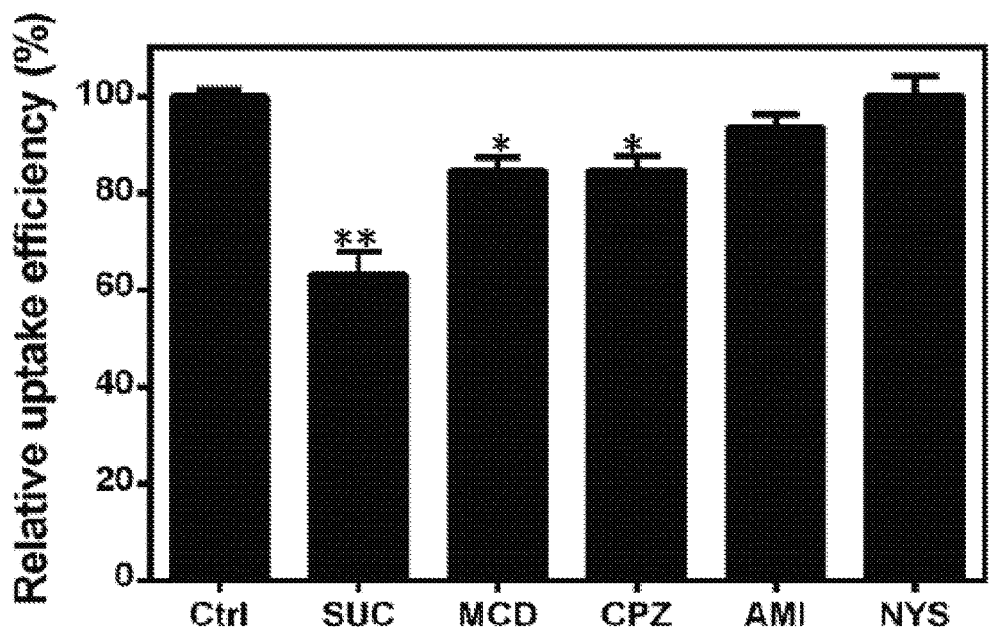
FIG. 10 shows relative uptake efficiency of TRAIL-Dox-PM-NG on MDA-MB-231 cells in the presence of various endocytosis inhibitors. Error bars indicate s.d. (n=3). *P<0.05, **P<0.01 compared with the control group (two-tailed Student's t-test). Inhibitor of clathrin-mediated endocytosis: sucrose (SUC) and chlorpromazine (CPZ); inhibitor of lipid raft: methyl-β-cyclodextrin (MCD); inhibitor of macropinocytosis: amiloride (AMI); inhibitor of caveolin-mediated endocytosis: nystatin (NYS).
Figure 11A:
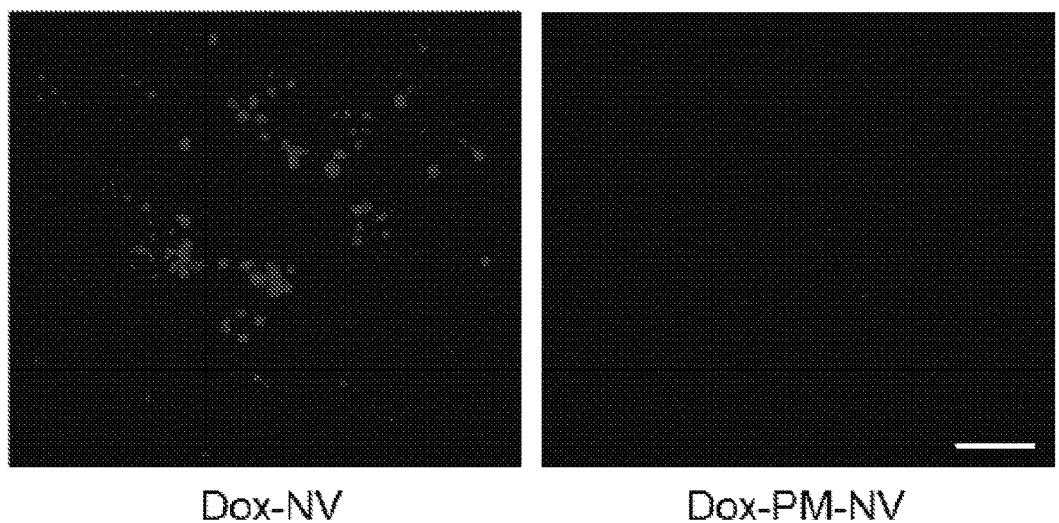
FIGS. 11A and 11B show the uptake of Dox-NV and Dox-PM-NV by Raw 264.7 cells.
Figure 11B:
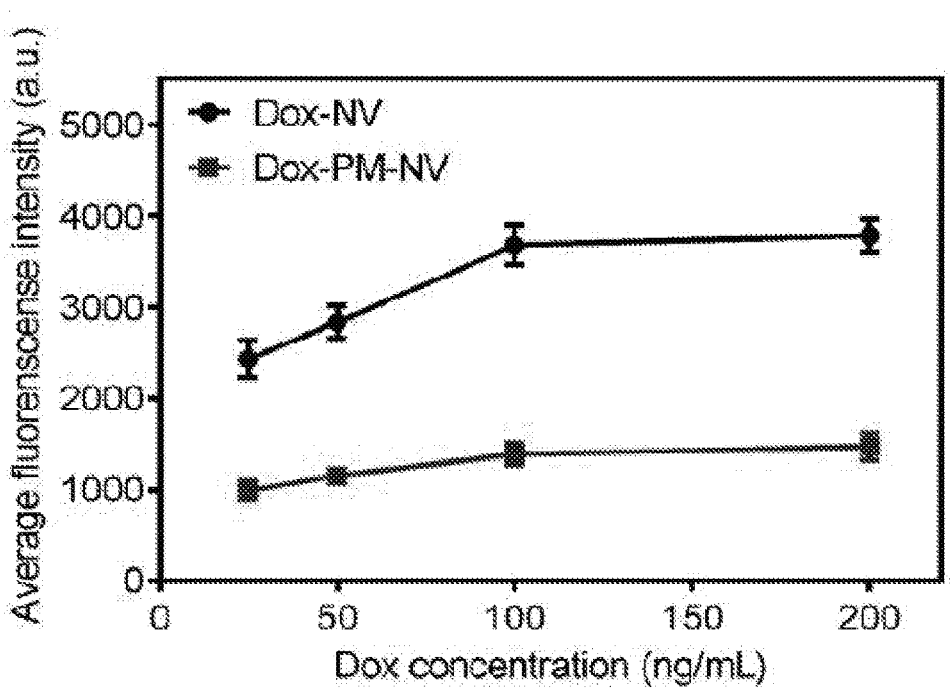

Next, the intracellular delivery of Dox by PM-NV was evaluated using CLSM. PM-NV was demonstrated to be internalized by the MDA-MB-231 cells via the clathrin-dependent endocytosis with the involvement of lipid raft (FIG. 10). As shown in FIG. 3C, the majority of the internalized PM-NV was found in the endo-lysosomes labeled with the green fluorescence, visualized by the overlaid yellow fluorescence for 1 h incubation. In contrast, a large number of endocytosed PM-NVs were localized in the nuclei stained with blue fluorescence, evidenced by the overlaid magenta fluorescence after 4 h incubation. The enhanced accumulation of Dox in the nuclei indicated the efficient nuclei delivery of Dox that was contributed by the dissociation of GDA matrix in the acidic endo-lysosome. Furthermore, the uptake efficiency of Dox-PM-NV on Raw 264.7 cells was significantly lower than that of Dox-NV, indicating the "self-recognized" proteins presented on PM could inhibit the uptake by macrophage cells, which is the main reason for quick clearance of drug delivery systems (DDS) in vivo (FIG. 11).

Figure 3D:
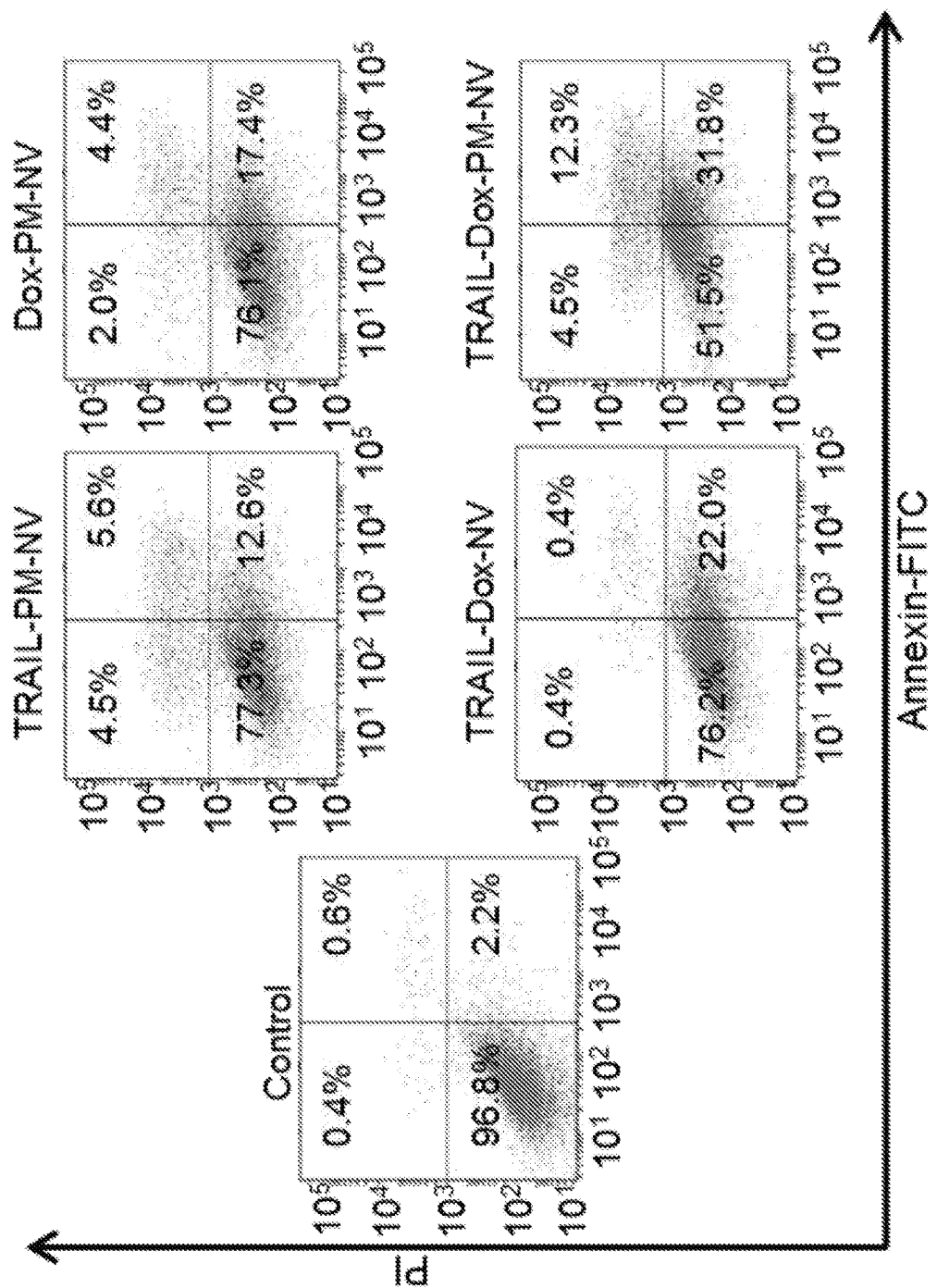

The terminal deoxynucleotidyl transferase dUTP nick end labeling (TUNEL) assay (Mo R, et al. (2014) Nat Commun. 5:3364) and the Annexin-V/PI double staining assay (Hu Q, et al. (2013) Biomaterials 34(4):1135-1145) were further applied to substantiate the synergetic apoptosis inducing capability of PM-NV. A stronger green fluorescence was visualized by TRAIL-Dox-PM-NV compared with TRAIL-Dox-NV, indicated the increased apoptotic DNA fragment (FIG. 3B). In addition, the quantitative flow cytometry results showed the rate of early and late apoptosis of MDAMB-231 cells after incubation with TRAIL-Dox-PM-NV for 12 h were 31.8% and 12.3%, respectively, which was significantly higher than 22.0% and 0.4% of TRAIL-Dox-NV, 17.4% and 4.4% of Dox-PM-NV, and 12.6% and 5.6% of TRAIL-PM-NV (FIG. 3D).

Figure 3E:
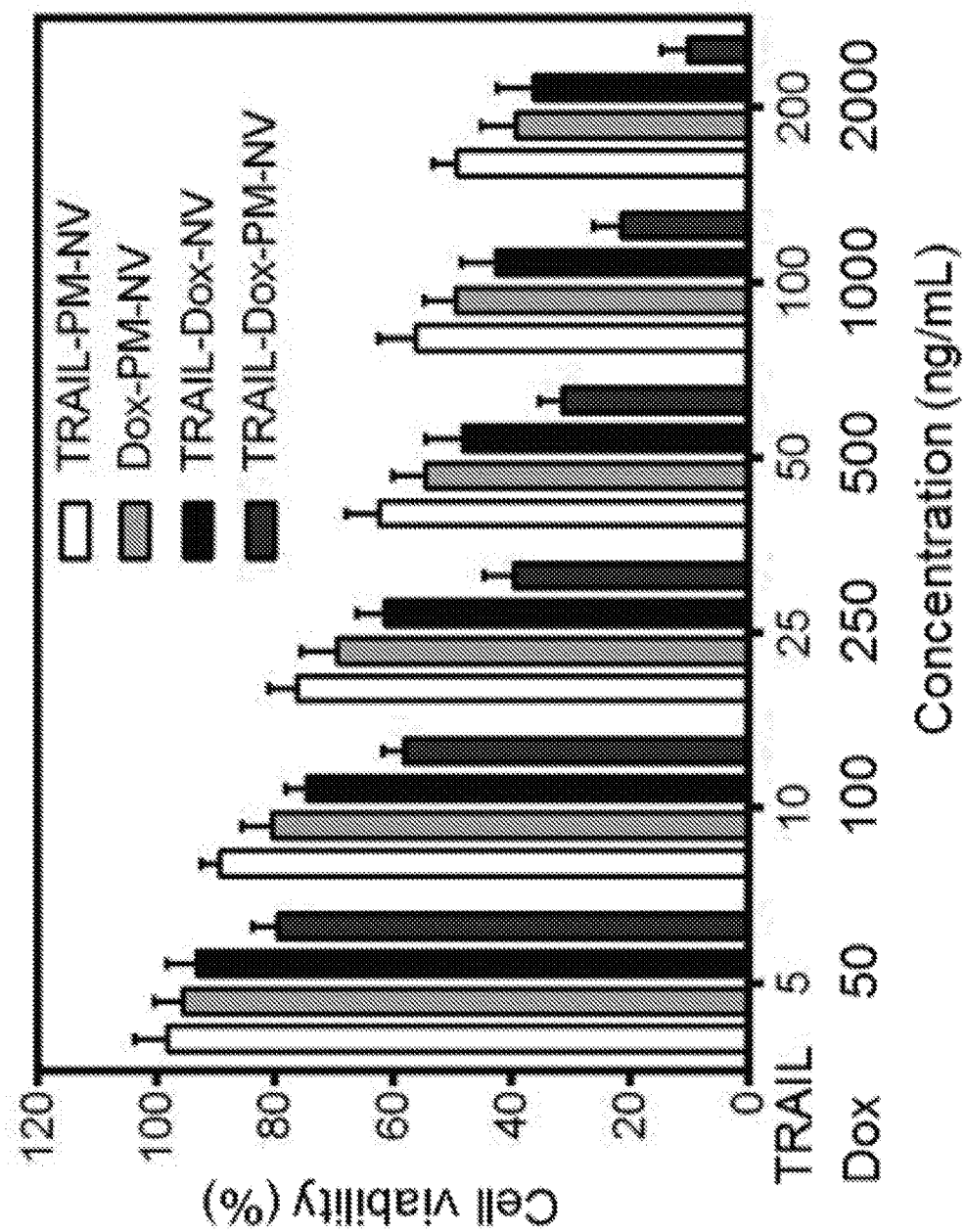

The in vitro cytotoxicity of TRAIL-Dox-PM-NV against MDA-MB-231 cells was evaluated by using the 3-(4,5-dimethylthiazol-2-yl)-2,5-diphenyltetrazolium bromide (MTT) assay (Mo R, et al. (2014) Nat Commun. 5:3364). TRAIL-Dox-PM-NV exhibited significantly enhanced cytotoxicity compared with TRAIL-Dox-NV, TRAIL-PM-NV and Dox-PM-NV at all studied TRAIL and Dox concentrations (FIG. 3E). Notably, the TRAIL-Dox-PM-NV exhibited the increased cytotoxicity with decreased $IC_{50}$ values of 20 ng/mL (TRAIL concentration) and 193 ng/mL (Dox concentration), 2.17-fold lower than that of TRAIL-Dox-NV, 2.61-fold lower than that of Dox-PM-NV, and 7.8-fold than that of TRAIL-PM-NV. Collectively, these results validated that the sequential and sit-specific delivery of TRAIL and Dox enabled by PM-NV effectively initiated a synergistic induction of apoptosis through the combination efficacy of TRAIL and Dox.

Figures 4A, 4B:
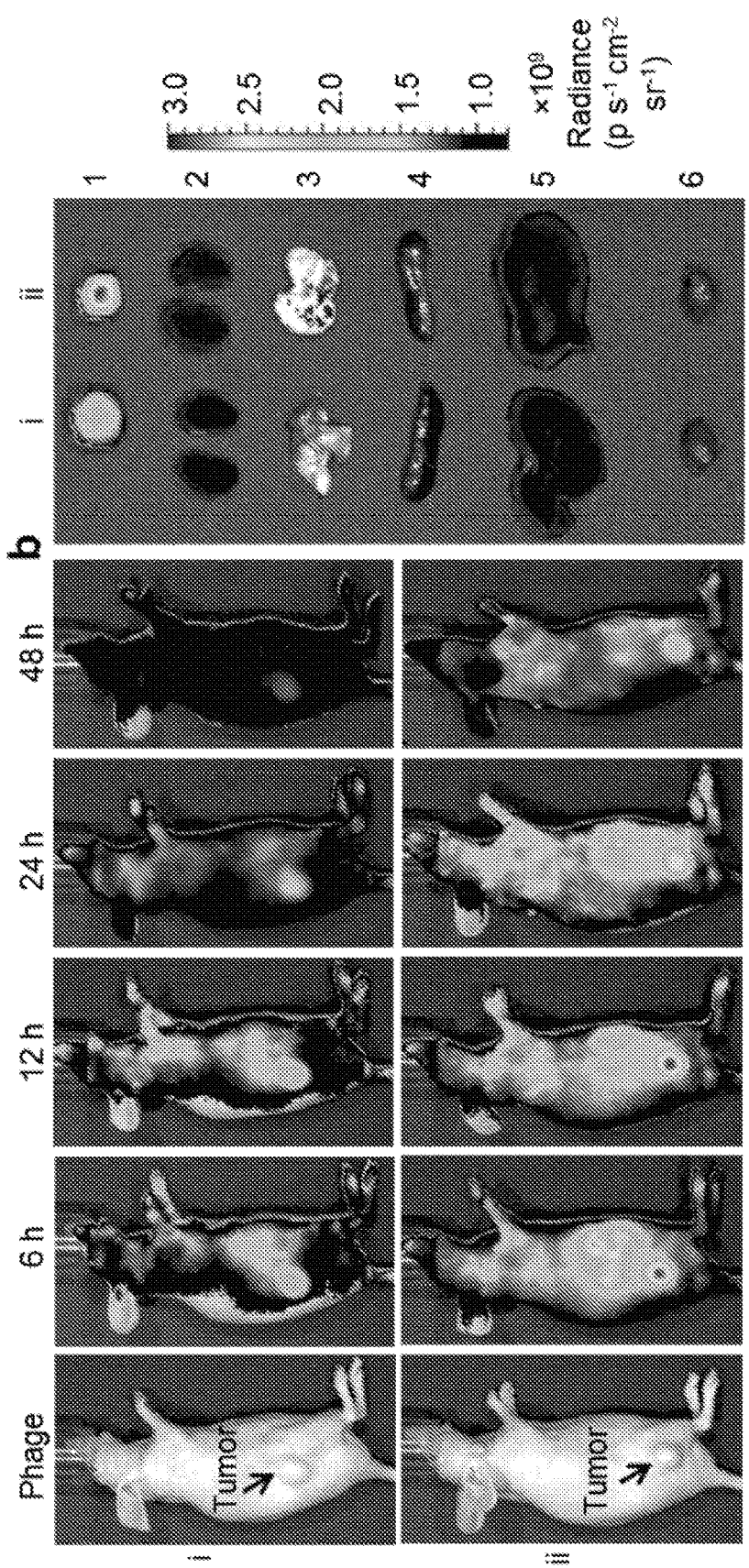
FIGS. 4A to 4D show in vivo targeting ability of PM-NV.
Figure 4C:
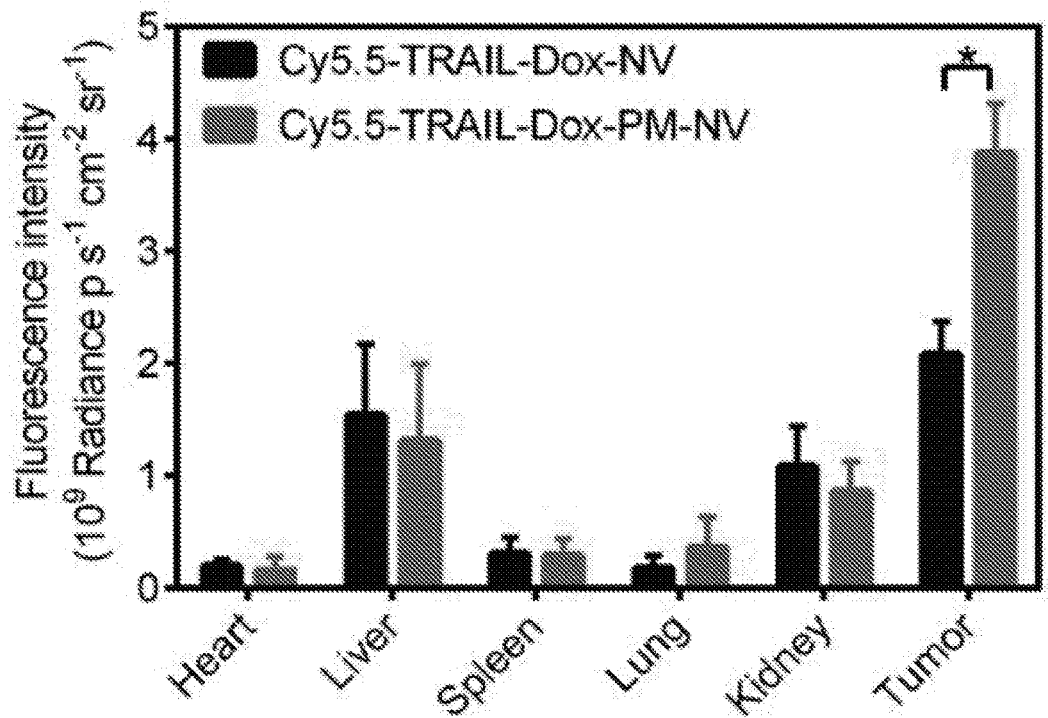
Figure 4D:
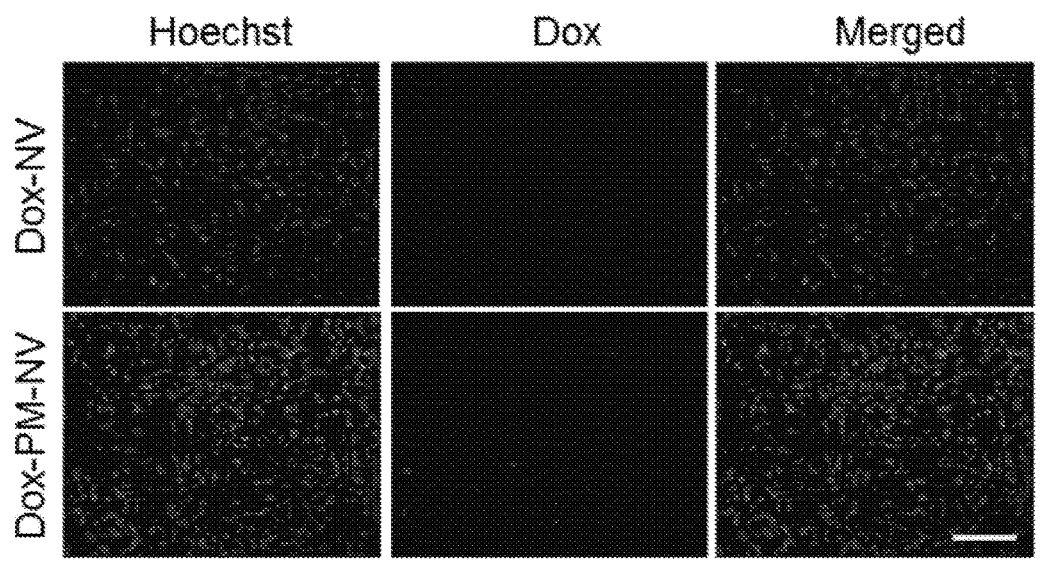
Figure 12A:
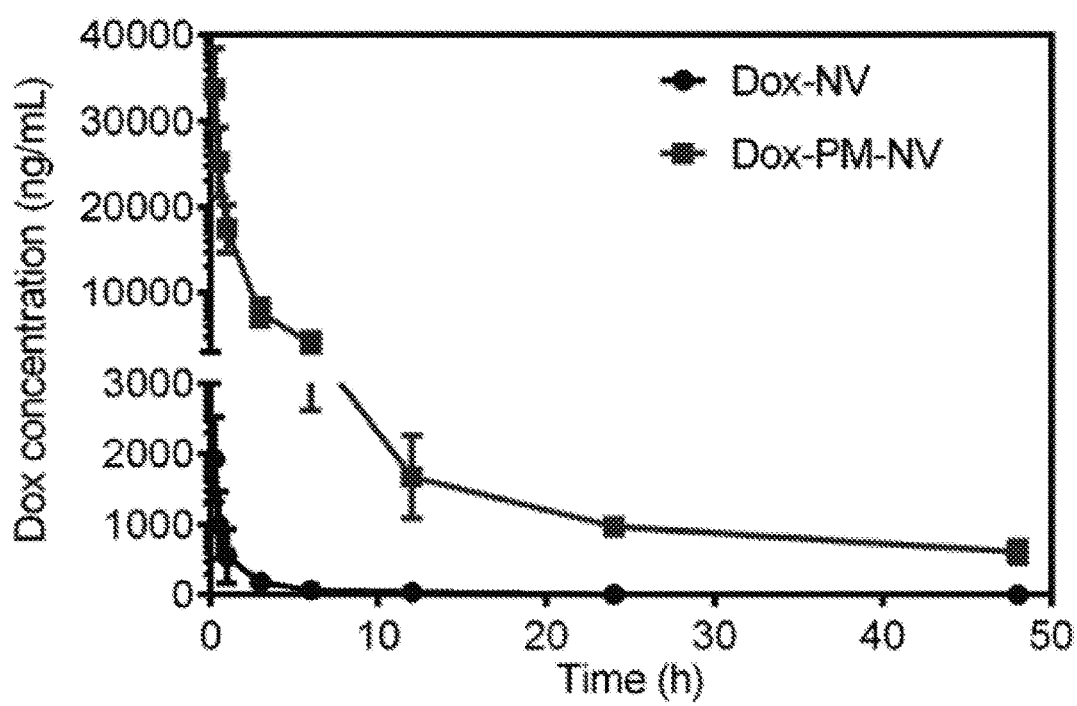
FIGS. 12A and 12B show pharmacokinetics of Dox after intravenous injection of the Dox-NV and Dox-PM-NV into mice at Dox dose of 5 mg/kg.

In vivo targeting capability and antitumor efficacy of PM-NV. To evaluate the tumor targeting capability of PM-NV, Cy5.5-labeled TRAIL-Dox-PM-NV was administrated intravenously into the MDA-MB-231 tumor-bearing nude mice via tail vein. PM-NV exhibited strong fluorescence signal at the tumor site at 6 h post-injection (FIG. 4a), validating the notable targeting ability of PM-NV, which can selectively bind to the overexpressed CD44 receptors on the surface of MDA-MB-231 cells. As time extended, elevated fluorescence intensity was found at the tumor site of mice treated with PM-NV when compared with that treated with NV at 12 h, 24 h and 48 h (FIG. 4A), indicating superiority of the active targeting capability mediated by platelet membranes than EPR effect. Additionally, a prolonged retention time at tumor site was achieved by PM-NV at 48 h post injection. After 48 h imaging, the tumor and normal tissues were taken out for ex vivo imaging. The fluorescence intensity of PM-NV at tumor site was much higher than that of NV and other organs (FIG. 4B). The results were confirmed by the quantitative region-of-interest (ROI) analysis, which showed 1.9-fold higher fluorescence intensity than that of NV, as well as 3.0-fold and 4.5-fold higher than that of liver and kidney (FIG. 4C). Additionally, the enhanced accumulation of PM-NV at tumor site was further validated by the distribution of Dox, which displayed the increased red fluorescence signal of Dox when compared with NV (FIG. 4E). The pharmacokinetics of PMNV administered intravenously was evaluated by quantitatively monitoring the Dox concentration in the blood plasma. The elimination half-life ($t_{1/2}$) and the AUC (area under the curve) were significantly higher than those of the NV, suggesting the capability of PM-NV to maintain a prolonged circulation time (FIG. 12). These in vivo findings further confirmed that the NV coated with the platelet membranes that contained "self-recognized" proteins (Hu C-M J, et al. (2011) Proc Natl Acad Sci USA. 108(27):10980-10985) could inhibit macrophage uptake, which was in good accordance with in vitro macrophage uptake results.

Figure 5A:
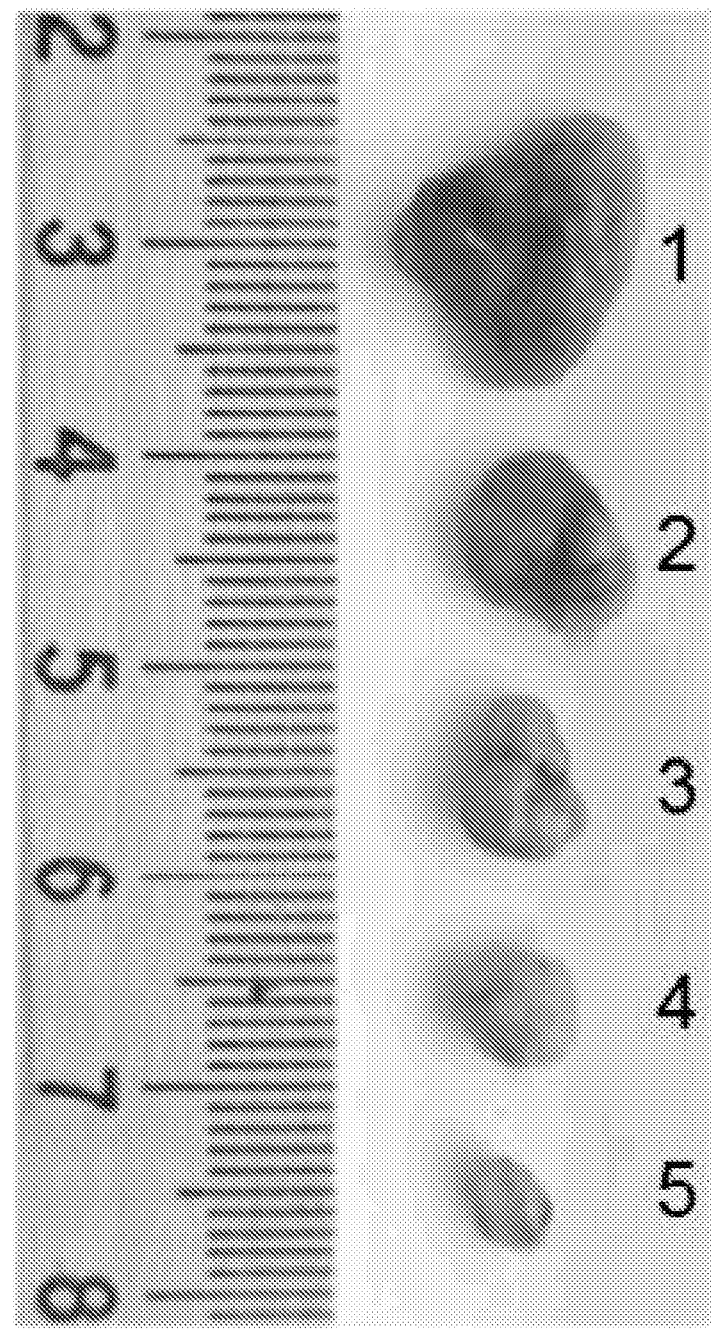
FIGS. 5A to 5D show in vivo antitumor efficacy evaluation.
Figure 5B:
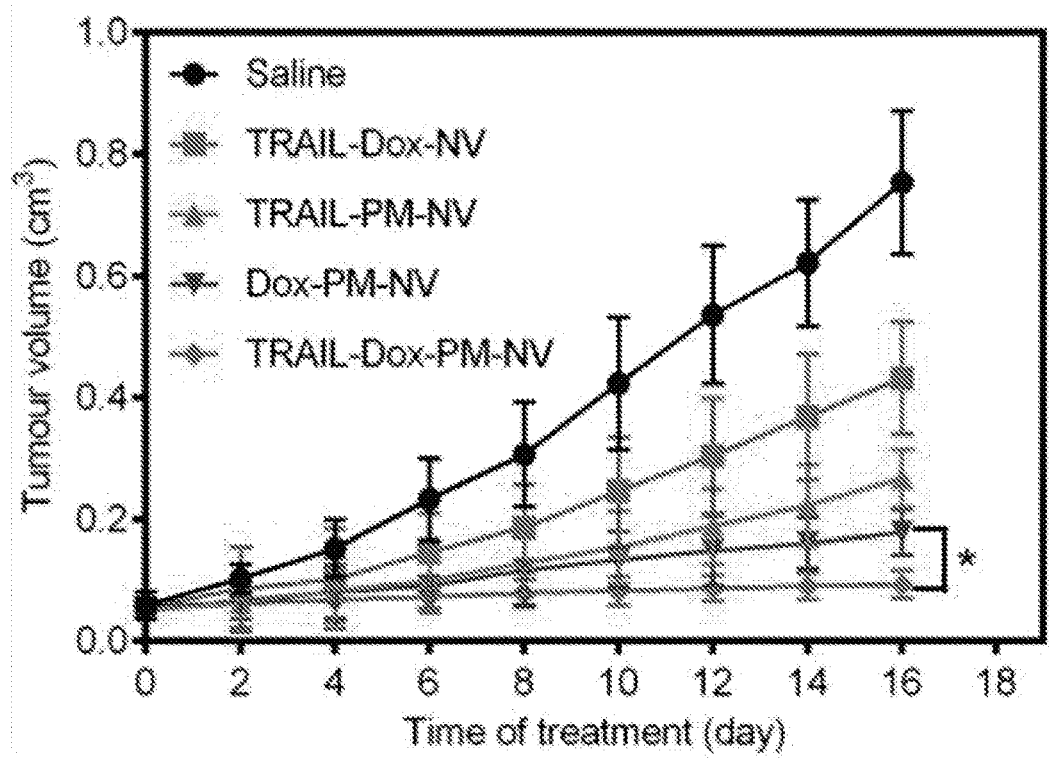
Figure 5C:
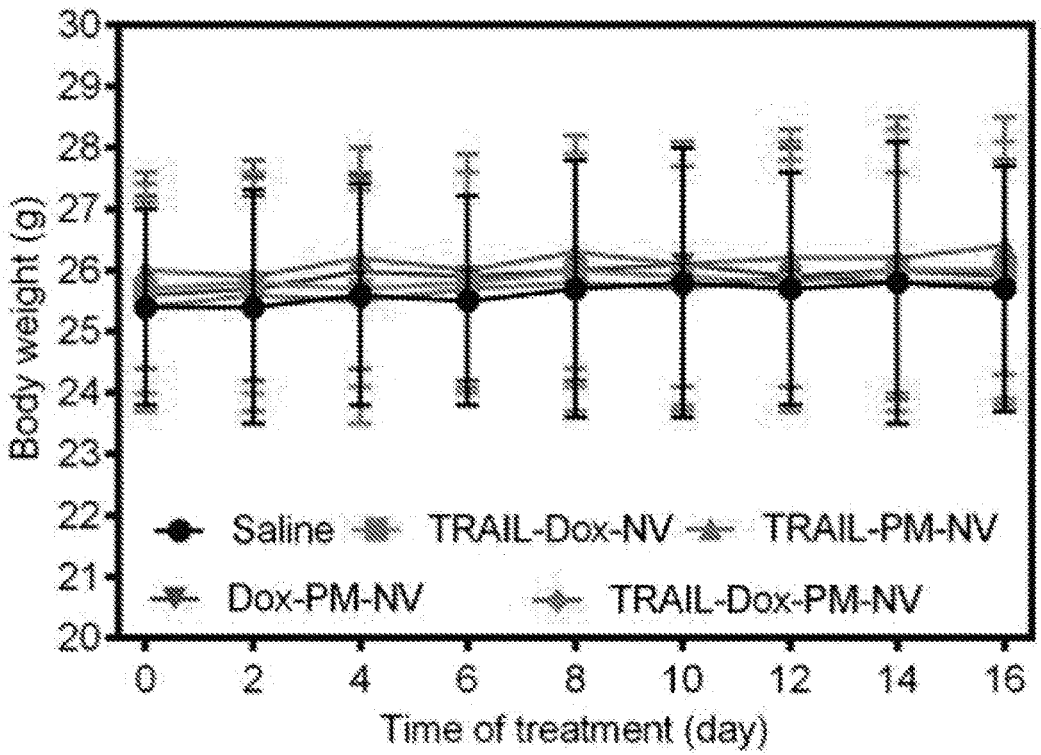
Figure 5D:
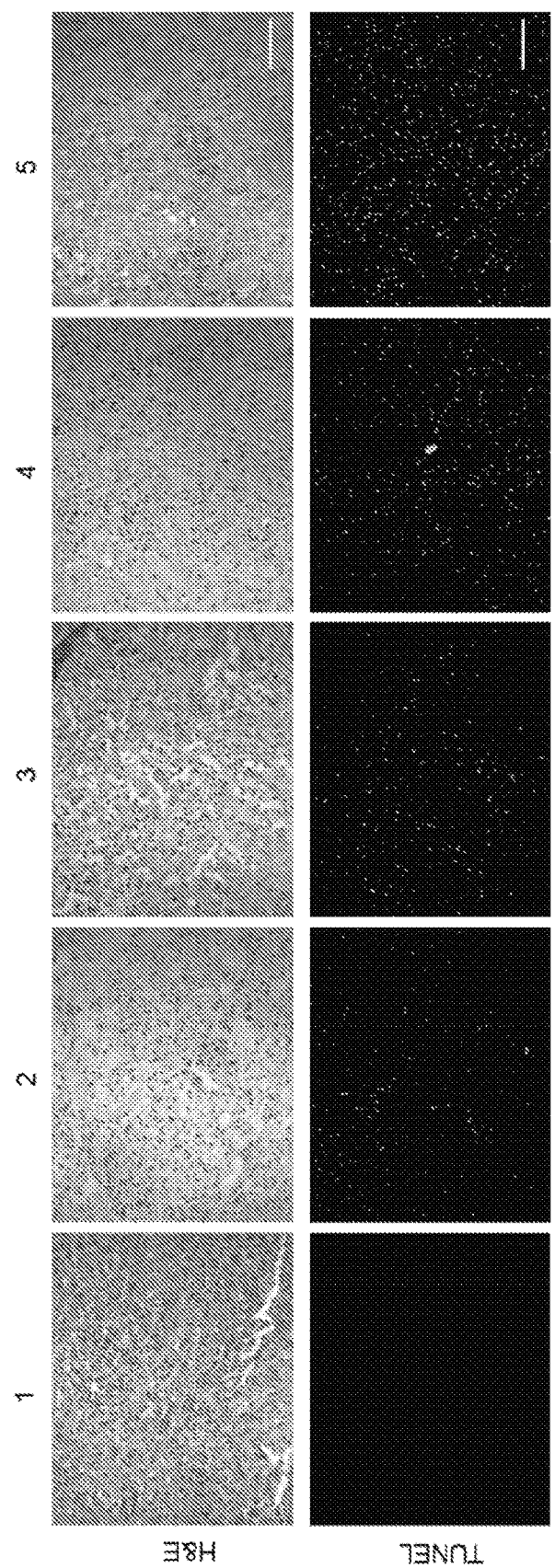
Figures 12B, 13:
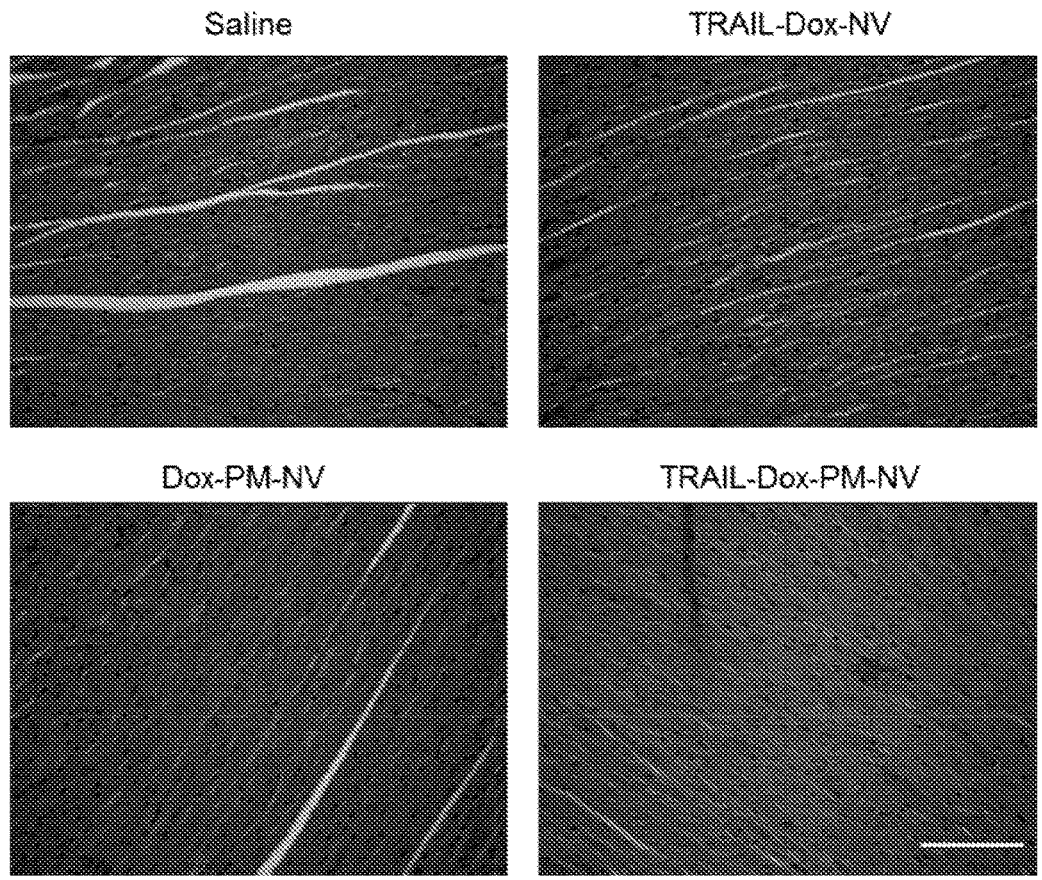
FIG. 13 shows histological observation of the heart tissues after the treatment with different Dox formulations. The heart sections were stained with hematoxylin and eosin (H&E). Scale bar: 200 μm.
Figure 14:
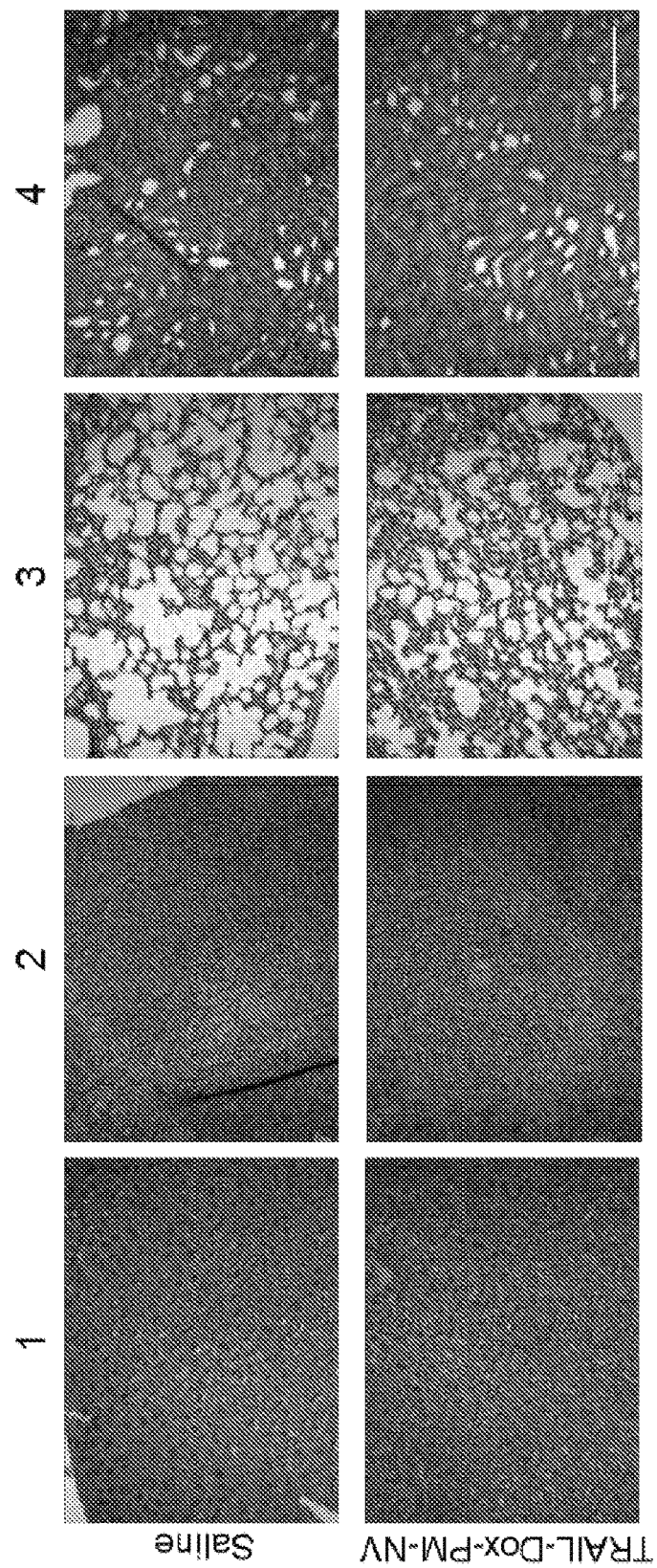
FIG. 14 shows histological observation of the organs collected from the MDA-MB-231 tumor-bearing mice after the treatment at day 16. The organ sections were stained with H&E. The numeric label for each organ is as follows: 1, Liver; 2, Spleen; 3, Lung; 4, Kidney. Scale bar: 100 µm.

The in vivo antitumor efficacy was then assessed using the MDA-MB-231 tumor-bearing nude mice. The growth of the tumor was significantly inhibited after the treatment with different TRAIL/Dox formulations, including TRAIL-Dox-NV, TRAIL-PM-NV, Dox-PM-NV and TRAIL-Dox-PM-NV, compared with the saline control group (FIG. 5A, 5B). The tumor treated with TRAIL-Dox-PM-NV showed the remarkably smaller volume compared with TRAIL-PM-NV and Dox-PM-NV, which indicated the synergetic antitumor efficacy enabled by PM-NV with the combination of TRAIL and Dox. Additionally, the strongest antitumor effect achieved by TRAIL-Dox-PM-NV suggested the sequential and site-specific delivery of TRAIL and Dox to their most active destinations could strengthen the synergetic antitumor efficacy. Meanwhile, the body weight of mice receiving different drug formulations remained stable during the treatment (FIG. 5C). The histologic images of the tumor section stained by the hematoxylin and eosin (H&E) showed a massive cancer cell remission after treated with TRAIL-Dox-PM-NV (FIG. 5d), while no obvious pathological abnormalities were observed on normal organs (FIG. 14). Moreover, no obvious pathological abnormalities in the heart, such as cardiomyopathy, the main toxic effect in Dox cancer treatment, were found for TRAIL-Dox-NV, Dox-PM-NV and TRAIL-Dox-PM-NV (FIG. 13). In addition, the fluorescence images obtained using the in situ TUNEL assay presented the highest level of cell apoptosis in the tumor collected from the mice treated with TRAIL-Dox-PM-NV (FIG. 5D).

Figures 6A, 6B:
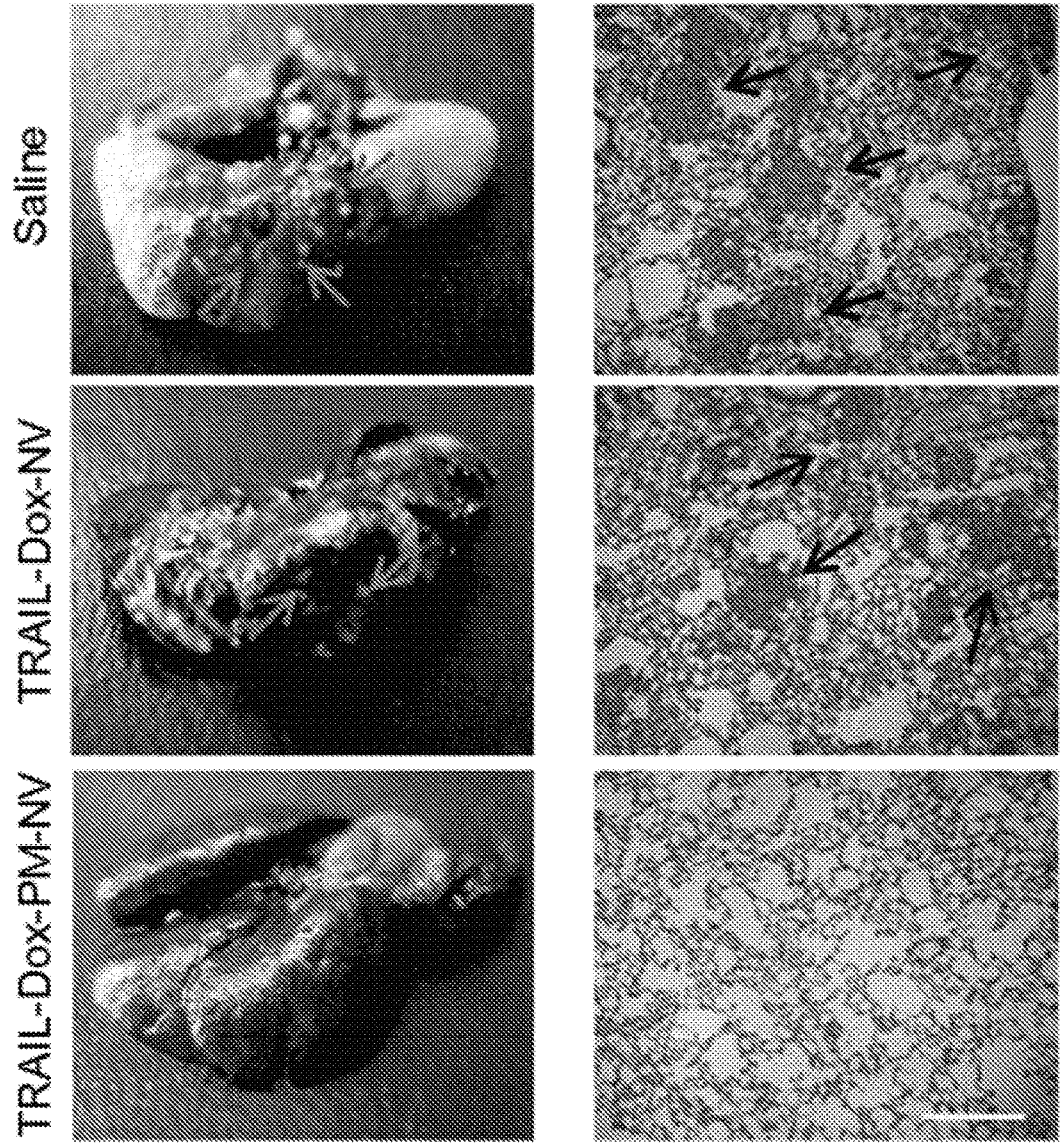
FIGS. 6A to 6C show in vivo elimination of circulating tumor cells (CTCs).
Figure 6C:
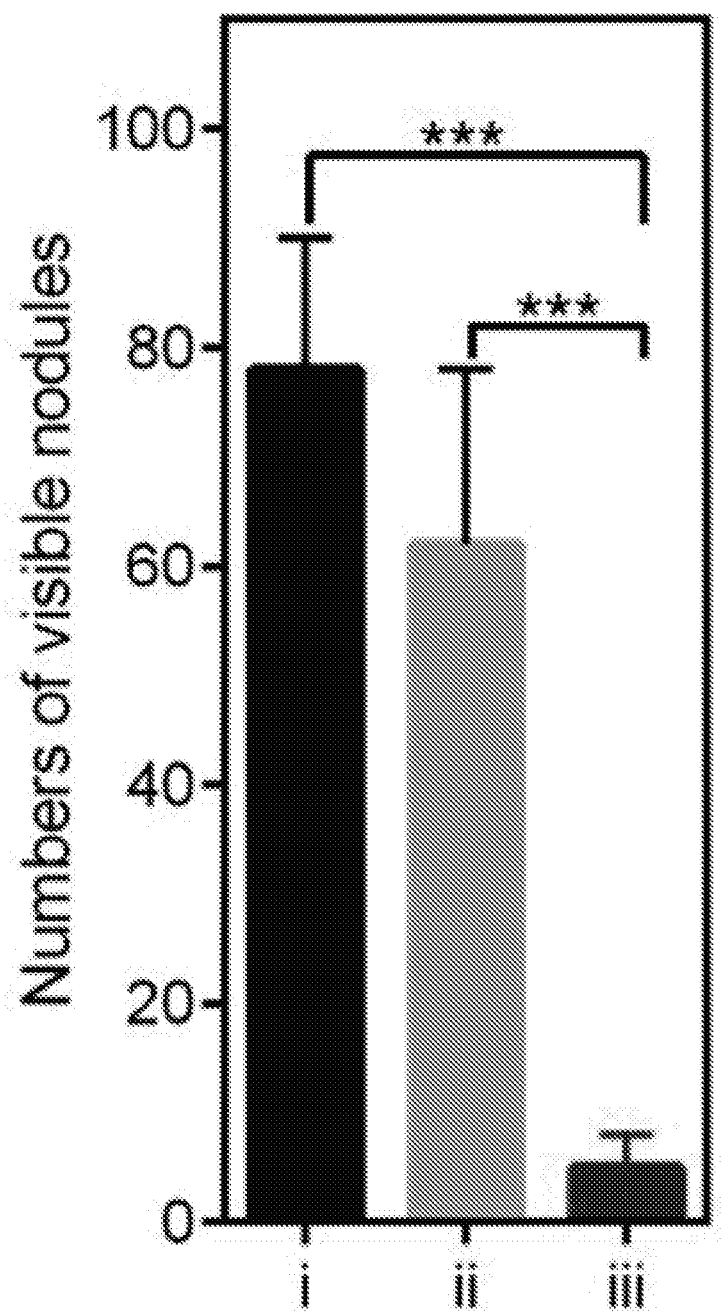

In vivo elimination of circulating tumor cells (CTCs) by PM-NV. To further assess the potency of this PM-coated combinational drug delivery platform, the in vivo capability of elimination of CTCs was investigated by injecting nude mice with MDA-MB-231 cells ($1\times10^6$ cells/100 µL saline). These circulating tumor cells could spread to various organs particularly into lungs (Price J E, et al. (1990) Cancer Res. 50(3):717-721). As displayed in FIGS. 6A and 6C, the mice treated with saline exhibited remarkable lung metastasis, as visualized by the metastatic nodules. However, the mice treated with TRAIL-Dox-NV showed slightly decrease in lung metastasis with no significant difference compared with the saline group. In sharp contrast, the remarkably reduced metastatic nodules were found at the lung of mice treated with TRAIL-Dox-PM-NV, Which was further confirmed by the H&E staining (FIG. 6B), suggesting the efficient elimination of CTCs in the blood stream which was attributed to the selective capture by P-Selectin on PM and subsequent activation of apoptosis by the binding of TRAIL and death receptors and accumulation of Dox into the nuclei (Mitchell M J, et al. (2014) Proc Natl Acad Sci USA. 111(3):930-935).

In conclusion, a platelet membrane-coated nano-formulation has been developed for sequential and site-specific delivery of TRAIL and Dox. By taking advantage of the specific affinity between platelets and cancer cells, the PM-NV can efficiently deliver TRAIL toward cancel cell membrane to activate the extrinsic apoptosis signaling pathway. Equipped with an acid-responsive encapsulation matrix, the PM-NV can be digested after endocytosis and enhanced the Dox accumulation at the nuclei for activation of the intrinsic apoptosis pathway. The promising synergetic antitumor efficacy was achieved by TRAIL-Dox-PM-NV. Because of the serum stability, targeting specificity, and ease of generation, this PM-NV could also deliver other proteins that act on the tumor cellular membrane, such as cetuximab and trastuzumab to achieve a synergetic antitumor efficacy, with combination of other intracellular therapeutics. Importantly, since the metastatic cancer cells need platelets to aggregate around them to help cancer cells survive in blood and spread to new tissues (Borsig L, et al. (2001) Proc Natl Acad Sci USA. 98(6):3352-3357; Borsig L (2008) Expert Rev Anticancer Ther. 8(8):1247-55), this PM-NV could further be adapted to identify and eliminate tumor cells that have the metastasis potentiality. Finally, since platelets also play a key role in several physiologic and pathologic processes such as hemostasis and thrombosis by forming the plugs that seal injured vessels and arrest bleeding (Ruggeri Z M (2002) Nat Med. 8(11):1227-1234; Davi G & Patrono C (2007) N Engl J Med. 357(24):2482-2494), this platform also holds promise in treating vascular disease.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A platelet membrane-coated nanovehicle, comprising
a) an inner core comprising a drug delivery matrix, wherein the drug delivery matrix comprises an antineoplastic therapeutic agent; and
b) an outer shell platelet membrane coating the inner core, wherein the outer shell platelet membrane further comprises tumor necrosis factor (TNF)-related apoptosis inducing ligand (TRAIL) and endogenous P-selectin protein.

2. The platelet membrane-coated nanovehicle of claim 1, wherein the antineoplastic drug is a hydrophobic small molecule.

3. The platelet membrane-coated nanovehicle of claim 2, wherein the anti-neoplastic drug is selected from the group consisting of paclitaxel, camptothecin, and docetaxel.

4. The platelet membrane-coated nanovehicle of claim 1, wherein the antineoplastic drug is a hydrophilic small molecule.

5. The platelet membrane-coated nanovehicle of claim 1, wherein the antineoplastic drug is selected from the group consisting of doxorubicin, cisplatin, and 5-fluorouracil.

6. The platelet membrane-coated nanovehicle of claim 1, wherein the outer shell platelet membrane comprises integrin $\alpha_{IIb}\beta_3$.

7. The platelet membrane-coated nanovehicle of claim 1, wherein the outer shell platelet membrane comprises a self-recognized immunomodulatory protein selected from the group consisting of CD47, CD55, and CD59.

8. The platelet membrane-coated nanovehicle of claim 1, wherein the outer shell platelet membrane further comprises a heterologous extracellularly active protein.

9. The platelet membrane-coated nanovehicle of claim 8, wherein the extracellularly active protein comprises a therapeutic antibody.

10. The platelet membrane-coated nanovehicle of claim 9, wherein the therapeutic antibody comprises cetuximab, trastuzumab, or a combination thereof.

11. The platelet membrane-coated nanovehicle of claim 1, wherein the drug delivery matrix further comprises a polymeric gel.

12. The platelet membrane-coated nanovehicle of claim 1, wherein the drug delivery matrix further comprises an inorganic particle.

13. The platelet membrane-coated nanovehicle of claim 1, wherein the drug delivery matrix further comprises a lipid particle.

14. The platelet membrane-coated nanovehicle of claim 1, wherein the drug delivery matrix further comprises a dendrimer particle.

15. A method comprising administering the platelet membrane-coated nanovehicle of claim 1 to a subject.

16. The method of claim 15, wherein the subject is suffering from cancer.

17. The method of claim 15, wherein the subject is suffering from a vascular disease.

* * * * *